(12) United States Patent
Ortyn et al.

(10) Patent No.: US 7,889,263 B2
(45) Date of Patent: Feb. 15, 2011

(54) SYSTEM AND METHOD FOR HIGH NUMERIC APERTURE IMAGING SYSTEMS

(75) Inventors: William E. Ortyn, Bainbridge Island, WA (US); David A. Basiji, Seattle, WA (US); David J. Perry, Woodinville, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 12/754,504

(22) Filed: Apr. 5, 2010

(65) Prior Publication Data

US 2010/0188559 A1 Jul. 29, 2010

Related U.S. Application Data

(62) Division of application No. 11/338,477, filed on Jan. 24, 2006, now Pat. No. 7,719,598, which is a division of application No. 09/977,076, filed on Oct. 12, 2001, now Pat. No. 7,009,651.

(60) Provisional application No. 60/240,125, filed on Oct. 12, 2000.

(51) Int. Cl.
*H04N 5/225* (2006.01)

(52) U.S. Cl. ...................................... 348/335; 348/345

(58) Field of Classification Search ................ 348/335, 348/345, 351; 356/124; 382/128
See application file for complete search history.

(56) References Cited

U.S. PATENT DOCUMENTS

| | | | |
|---|---|---|---|
| 3,497,690 A | 2/1970 | Wheeless, Jr. et al. ... | 250/461.2 |
| 3,555,280 A | 1/1971 | Richards, Jr. ................ | 250/201 |
| 3,586,760 A | 6/1971 | Dillenburger ................ | 348/339 |
| 3,922,069 A | 11/1975 | Kishikawa et al. .......... | 350/173 |
| 4,313,734 A | 2/1982 | Leuvering .................... | 23/230 |
| 4,414,575 A * | 11/1983 | Yamamoto et al. .......... | 348/350 |
| 4,635,293 A | 1/1987 | Watanabe .................... | 382/44 |

(Continued)

FOREIGN PATENT DOCUMENTS

EP 0 154 404 9/1985

(Continued)

OTHER PUBLICATIONS

Hecht, Eugene. "Optics 4$^{th}$ ed." Addison-Wesley Longman, Inc., XP-002465391, ISBN: 0-8053-8566-5, 2002.

(Continued)

*Primary Examiner*—Tuan Ho
(74) *Attorney, Agent, or Firm*—Ronald M. Anderson

(57) ABSTRACT

A system and method for high numeric aperture imaging systems includes a splitter, a defocusing system, and a combiner. The splitter reflects a portion of collected light and transmits another portion of the collected light. The defocusing system is configured to modify optical power of either the transmitted portion or reflected portion of the collected light. The combiner is oriented with respect to a mechanical angle. The combiner recombines portions of the transmitted portion and the reflected portion such that the transmitted portion and reflected portion are subsequently transmitted being separated by an optical separation angle based upon the mechanical angle of orientation of the combiner. Various other implementations are used to maintain focus with regards to the imaging systems involved.

4 Claims, 27 Drawing Sheets

U.S. PATENT DOCUMENTS

| | | | |
|---|---|---|---|
| 4,662,742 A | 5/1987 | Chupp | 356/39 |
| 4,677,680 A | 6/1987 | Harima et al. | 382/1 |
| 4,703,017 A | 10/1987 | Campbell et al. | 436/501 |
| 4,737,932 A | 4/1988 | Baba | 364/900 |
| 4,770,992 A | 9/1988 | Van den Engh et al. | 435/6 |
| 4,777,525 A | 10/1988 | Preston, Jr. | 358/102 |
| 4,786,165 A | 11/1988 | Yamamoto et al. | 356/23 |
| 4,845,197 A | 7/1989 | Petersen et al. | 530/387 |
| 4,857,453 A | 8/1989 | Ullman et al. | 435/7 |
| 5,096,807 A | 3/1992 | Leaback | 435/6 |
| 5,122,453 A | 6/1992 | Martin et al. | 435/7.24 |
| 5,141,609 A | 8/1992 | Sweedler et al. | 204/180.1 |
| 5,153,916 A | 10/1992 | Inagaki et al. | 382/4 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/134 |
| 5,247,339 A | 9/1993 | Ogino | 356/73 |
| 5,247,340 A | 9/1993 | Ogino | 356/73 |
| 5,257,182 A | 10/1993 | Luck et al. | 364/413.1 |
| 5,272,354 A | 12/1993 | Kosaka | 250/574 |
| 5,351,311 A | 9/1994 | Rogers et al. | 382/45 |
| 5,372,936 A | 12/1994 | Fraatz et al. | 435/34 |
| 5,422,712 A | 6/1995 | Ogino | 356/73 |
| 5,436,144 A | 7/1995 | Stewart et al. | 435/91.2 |
| 5,444,527 A | 8/1995 | Kosaka | 356/73 |
| 5,459,240 A | 10/1995 | Foxwell et al. | 530/328 |
| 5,471,294 A | 11/1995 | Ogino | 356/73 |
| 5,548,349 A | 8/1996 | Mizuguchi et al. | 348/766 |
| 5,548,395 A | 8/1996 | Kosaka | 356/73 |
| 5,568,315 A | 10/1996 | Shuman | 359/487 |
| 5,596,401 A | 1/1997 | Kusuzawa | 356/23 |
| 5,621,460 A | 4/1997 | Hatlestad et al. | 348/265 |
| 5,625,048 A | 4/1997 | Tsien et al. | 536/23.4 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,686,960 A | 11/1997 | Sussman et al. | 348/335 |
| 5,695,934 A | 12/1997 | Brenner | 435/6 |
| 5,733,721 A | 3/1998 | Hemstreet, III et al. | 435/6 |
| 5,754,291 A | 5/1998 | Kain | 356/338 |
| 5,760,899 A | 6/1998 | Eismann | 356/456 |
| 5,764,792 A | 6/1998 | Kennealy | 382/133 |
| RE35,868 E | 8/1998 | Kosaka | 250/574 |
| 5,828,776 A | 10/1998 | Lee et al. | 382/133 |
| 5,831,723 A | 11/1998 | Kubota et al. | 356/73 |
| 5,844,670 A | 12/1998 | Morita et al. | 356/124 |
| 5,848,123 A | 12/1998 | Strommer | 378/98.8 |
| 5,855,753 A | 1/1999 | Trau et al. | 204/484 |
| 5,900,942 A | 5/1999 | Spiering | 356/400 |
| 5,926,283 A | 7/1999 | Hopkins | 356/419 |
| 5,929,986 A | 7/1999 | Slater et al. | 356/326 |
| 5,959,953 A | 9/1999 | Alon | 369/44.41 |
| 5,985,549 A | 11/1999 | Singer et al. | 435/6 |
| 5,986,061 A | 11/1999 | Pestka | 530/352 |
| 6,007,994 A | 12/1999 | Ward et al. | 435/6 |
| 6,007,996 A | 12/1999 | McNamara et al. | 435/6 |
| 6,014,468 A | 1/2000 | McCarthy et al. | 382/254 |
| 6,066,459 A | 5/2000 | Garini et al. | 435/6 |
| 6,108,082 A | 8/2000 | Pettipiece et al. | 356/301 |
| 6,116,739 A | 9/2000 | Ishihara et al. | 353/31 |
| 6,156,465 A | 12/2000 | Cao et al. | 430/30 |
| 6,159,686 A | 12/2000 | Kardos et al. | 435/6 |
| 6,210,973 B1 | 4/2001 | Pettit | 436/172 |
| 6,211,955 B1 | 4/2001 | Basiji et al. | 356/326 |
| 6,229,913 B1 | 5/2001 | Nayar et al. | 382/154 |
| 6,249,314 B1 | 6/2001 | Yamamoto et al. | 348/242 |
| 6,249,341 B1 | 6/2001 | Basiji et al. | 356/73 |
| 6,256,096 B1 | 7/2001 | Johnson | 356/335 |
| 6,259,807 B1 | 7/2001 | Ravkin | 381/133 |
| 6,330,081 B1 | 12/2001 | Scholten | 358/463 |
| 6,330,361 B1 | 12/2001 | Mitchell et al. | 382/211 |
| 6,381,363 B1 | 4/2002 | Murching et al. | 382/164 |
| 6,473,176 B2 | 10/2002 | Basiji et al. | 356/326 |
| 6,507,391 B2 | 1/2003 | Riley et al. | 356/28 |
| 6,510,319 B2 | 1/2003 | Baum et al. | 455/442 |
| 6,519,355 B2 | 2/2003 | Nelson | 382/133 |
| 6,522,781 B1 | 2/2003 | Norikane et al. | 382/203 |
| 6,532,061 B2 | 3/2003 | Ortyn et al. | 356/28 |
| 6,548,259 B2 | 4/2003 | Ward et al. | 435/6 |
| 6,549,664 B1 | 4/2003 | Daiber et al. | 382/232 |
| 6,563,583 B2 | 5/2003 | Ortyn et al. | 356/400 |
| 6,580,504 B1 | 6/2003 | Basiji et al. | 356/338 |
| 6,583,865 B2 | 6/2003 | Basiji et al. | 356/73 |
| 6,608,680 B2 | 8/2003 | Basiji et al. | 356/338 |
| 6,608,682 B2 | 8/2003 | Ortyn et al. | 356/419 |
| 6,618,140 B2 | 9/2003 | Frost et al. | 356/317 |
| 6,620,591 B1 | 9/2003 | Dunlay et al. | 435/7.2 |
| 6,658,143 B2 | 12/2003 | Hansen et al. | 382/133 |
| 6,671,044 B2 | 12/2003 | Ortyn et al. | 356/326 |
| 6,671,624 B1 | 12/2003 | Dunlay et al. | 702/19 |
| 6,707,551 B2 | 3/2004 | Ortyn et al. | 356/338 |
| 6,716,588 B2 | 4/2004 | Sammak et al. | 435/7.23 |
| 6,727,066 B2 | 4/2004 | Kaser | 435/6 |
| 6,763,149 B2 | 7/2004 | Riley et al. | 382/294 |
| 6,778,263 B2 | 8/2004 | Ortyn et al. | 356/28 |
| 6,873,733 B2 | 3/2005 | Dowski, Jr. | 382/232 |
| 6,875,973 B2 | 4/2005 | Ortyn et al. | 250/201.3 |
| 6,906,792 B2 | 6/2005 | Ortyn et al. | 356/28.5 |
| 6,927,922 B2 | 8/2005 | George et al. | 359/708 |
| 6,934,408 B2 | 8/2005 | Frost et al. | 382/129 |
| 6,947,128 B2 | 9/2005 | Basiji et al. | 356/73 |
| 6,947,136 B2 | 9/2005 | Ortyn et al. | 356/338 |
| 6,975,400 B2 | 12/2005 | Ortyn et al. | 356/419 |
| 7,006,710 B2 | 2/2006 | Riley et al. | 382/294 |
| 7,033,819 B2 | 4/2006 | Kim et al. | 435/29 |
| 7,042,639 B1 | 5/2006 | McDowell | 359/398 |
| 7,050,620 B2 | 5/2006 | Heckman | 382/133 |
| 7,057,732 B2 | 6/2006 | Jorgenson et al. | 356/445 |
| 7,079,708 B2 | 7/2006 | Riley et al. | 382/294 |
| 7,087,877 B2 | 8/2006 | Ortyn et al. | 250/201.2 |
| 7,139,415 B2 | 11/2006 | Finkbeiner | 382/128 |
| 7,180,673 B2 | 2/2007 | Dowski, Jr. | 359/637 |
| 7,190,832 B2 | 3/2007 | Frost et al. | 382/173 |
| 7,221,457 B2 | 5/2007 | Jorgenson et al. | 356/445 |
| 7,289,205 B2 | 10/2007 | Yaroslavsky et al. | 356/417 |
| 7,315,357 B2 | 1/2008 | Ortyn et al. | 356/73 |
| 7,567,695 B2 | 7/2009 | Frost et al. | 382/129 |
| 7,667,761 B2 * | 2/2010 | Thomas | 348/335 |
| 2001/0006416 A1 | 7/2001 | Johnson | 356/73 |
| 2001/0012620 A1 | 8/2001 | Rich | 435/7.1 |
| 2002/0126275 A1 | 9/2002 | Johnson | 356/317 |
| 2002/0146734 A1 | 10/2002 | Ortyn et al. | 435/6 |
| 2003/0048931 A1 | 3/2003 | Johnson et al. | 382/128 |
| 2003/0049701 A1 | 3/2003 | Muraca | 435/7.23 |
| 2003/0059093 A1 | 3/2003 | Rosania et al. | 382/128 |
| 2003/0104439 A1 | 6/2003 | Finch | 435/6 |
| 2004/0093166 A1 | 5/2004 | Kil | 702/19 |
| 2004/0111220 A1 | 6/2004 | Ochs et al. | 702/19 |
| 2004/0241759 A1 | 12/2004 | Tozer et al. | 435/7.2 |
| 2005/0014129 A1 | 1/2005 | Cliffel et al. | 435/4 |
| 2006/0246481 A1 | 11/2006 | Finch et al. | 435/6 |
| 2006/0257884 A1 | 11/2006 | Brawley et al. | 435/6 |
| 2007/0054350 A1 | 3/2007 | Walker, Jr. | 435/34 |
| 2008/0240539 A1 | 10/2008 | George et al. | 382/133 |
| 2009/0202130 A1 | 8/2009 | George et al. | 382/133 |

FOREIGN PATENT DOCUMENTS

| | | |
|---|---|---|
| EP | 0 280 559 | 8/1988 |
| EP | 0 281 327 | 6/1993 |
| EP | 0 372 707 | 3/1996 |
| EP | 0 950 890 | 10/1999 |
| EP | 1 316 793 | 6/2003 |
| WO | WO 88/08534 | 11/1988 |

| WO | WO 90/10715 | 9/1990 |
| WO | WO 95/20148 | 7/1995 |
| WO | WO 97/26333 | 7/1997 |
| WO | WO 98/53093 | 11/1998 |
| WO | WO 98/53300 | 11/1998 |
| WO | WO 99/24458 | 5/1999 |
| WO | WO 99/64592 | 12/1999 |
| WO | WO 00/06989 | 2/2000 |
| WO | WO 00/14545 | 3/2000 |
| WO | WO 00/42412 | 7/2000 |
| WO | WO 01/11341 | 2/2001 |
| WO | WO 01/46675 | 6/2001 |
| WO | WO 02/17622 | 2/2002 |
| WO | WO 02/18537 | 3/2002 |
| WO | WO 02/35474 | 5/2002 |
| WO | WO 02/073200 | 9/2002 |
| WO | WO 02/079391 | 10/2002 |
| WO | WO 2005/090945 | 9/2005 |
| WO | WO 2005/098430 | 10/2005 |

OTHER PUBLICATIONS

Hultdin et al., "Telomere analysis by fluorescence *in situ* hybridization and flow cytometry," *Nucleic Acids Research* vol. 26, No. 16: 3651-3656, Aug. 15, 1998.

Kubota et al., "Flow Cytometer and Imaging Device Used in Combination." *Cytometry* 21: 129-132, 1995.

Kubota, Fumio. "Analysis of red cell and platelet morphology using an imaging-combined flow cytometer." *Clin. Lab. Haem.* 25: 71-76, 2003.

Lauzon et al., "Flow Cytometric Measurement of Telomere Length," *Cytometry* 42: 159-164, Jun. 2000.

Levron et al., "Sperm chromosome abnormalities in men with severe male factor infertility who are undergoing in vitro fertilization with intracytoplasmic sperm injection," *Fertility and Sterility* vol. 76, No. 3: 479-484, Sep. 2001.

Lowe et al., "Aneuploid epididymal sperm detected in chromosomally normal and Robertsonian translocation-bearing mice using a new three-chromosome FISH method," *Chromosoma* 105: 204-210, 1996.

Majno et al., "Apoptosis, Oncosis, and Necrosis *An Overview of Cell Death*," *American Journal of Pathology* vol. 146, No. 1: 3-15, Jan. 1, 1995.

Martin et al., "Detection of aneuploidy in human interphase spermatozoa by fluorescence in situ hybridization (FISH)," *Cytogenetics and Cell Genetics* 64: 23-26, 1993.

Nautiyal et al., "17β-Estradiol induces nuclear translocation of CrkL at the window of embryo implantation," *Biochemical and Biophysical Research Communications* 318: 103-112, 2004.

Ong, Sim Heng, "Development of a System for Imaging and Classifying Biological Cells in a Flow Cytometer," Doctor of Philosophy Thesis, University of Sydney, School of Electrical Engineering, Aug. 1985.

Ong et al., "Development of an Image Flow Cytometer," *Analytical and Quantitative Cytology and Histology*. XIVth International Conference on Medical and Biological Engineering and the VIIth International Conference on Medical Physics, Finland: 375-382, Aug. 1987.

Ong et al., "Optical Design in a Flow System For Imaging Cells," *Sciences in Medicine*, vol. 14, No. 2: 74-80, 1991.

Ong et al., "Analysis of MTF Degradation in the Imaging of Cells in a Flow System," *International Journal of Imaging Systems & Technology* 5: 243-250, 1994.

Ortyn et al., "Extended Depth of Field Imaging for High Speed Cell Analysis" *Cytometry Part A* 71A: 215-231, 2007.

Pala et al., "Flow cytometric measurement of intracellular cytokines," *Journal of Immunological Methods* 243: 107-124, 2000.

Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," *Human Reproduction* vol. 14, No. 5: 1266-1273, 1999.

Patterson et al., "Detection of HIV-1 DNA and Messenger RNA in Individual Cells by PCR-Driven in Situ Hybridization and Flow Cytometry," *Science* 260: 976-979, May 14, 1993.

Perreault et al., "The Role of Disulfide Bond Reduction during Mammalian Sperm Nuclear Decondensation *in Vivo*," *Developmental Biology* 101: 160-167, 1984.

Pinkel et al., "Cytogenetic analysis using quantitative, high sensitivity, fluorescence hybridization," *Proceedings of the National Academy of Sciences: Genetics* 83: 2934-2938, 1986.

Pollice et al., "Sequential Paraformaldehyde and Methanol Fixation for Simultaneous Flow Cytometric Analysis of DNA, Cell Surface Proteins, and Intracellular Proteins," *Cytometry* 13: 432-444, 1992.

Ried et al., "Simultaneous visualization of seven different DNA probes by *in situ* hybridization using combinatorial fluorescence and digital imaging microscopy," *Proceedings of the National Academy of Sciences: Genetics* 89: 1388-1392, Feb. 1992.

Robbins et al., "Aneuploidy in sperm of Hodgkin's disease patients receiving NOVP chemotherapy," *The American Journal of Human Genetics* vol. 55, No. 3—Supplement: A68 (371), Sep. 1994.

Robbins et al., "Detection of Aneuploid Human Sperm by Fluorescence In Situ Hybridization: Evidence for a Donor Difference in Frequency of Sperm Disomic for Chromosomes I and Y," *The American Journal of Human Genetics*, 52: 799-807, 1993.

Robbins et al., "Three-probe Fluorescence *in situ* Hybridization to Assess Chromosome X, Y, and 8 Aneuploidy in Sperm of 14 Men from Two Healthy Groups: Evidence for a Paternal Age Effect on Sperm Aneuploidy," *Reproduction, Fertility and Development* 7: 799-809, 1995.

Robbins et al., "Use of Fluorescence In Situ Hybridization (FISH) To Assess Effects of Smoking, Caffeine, and Alcohol on Aneuploidy Load in Sperm of Healthy Men," *Environmental and Molecular Mutagenesis* 30: 175-183, 1997.

Rufer et al., "Telomere length dynamics in human lymphocyte subpopulations measured by flow cytometry," *Nature Biotechnology* 16: 743-747, Aug. 1998.

Salzman et al., "Light Scatter: Detection and Usage," *Current Protocols in Cytometry Supplement* 9: 1.13.1-1.138.8, 1999.

Satoh et al., "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry* 48: 194-201, 2002.

Schmid et al., "Evaluation of inter-scorer and inter-laboratory reliability of the mouse epididymal sperm aneuploidy (m-ESA) assay," *Mutagenesis* vol. 16, No. 3: 189-195, 2001.

Schmid et al., "Simultaneous Flow Cytometric Analysis of Two Cell Surface Markers, Telomere Length, and DNA Content," *Cytometry* 49: 96-105, 2002.

Schwerin et al., "Quantification of Y Chromosome Bearing Spermatozoa of Cattle Using In Situ Hybridization," *Molecular Reproduction and Development* 30: 39-43, 1991.

Shi et al., "Aneuploidy in human sperm: a review of the frequency and distribution of aneuploidy, effects of donor age and lifestyle factors," *Cytogenetics and Cell Genetics* 90: 219-226, 2000.

Timm et al., "Amplification and Detection of a Y-Chromosome DNA Sequence by Fluorescence In Situ Polymerase Chain Reaction and Flow Cytometry Using Cells in Suspension," *Cytometry (Communications in Clinical Cytometry)* 22: 250-255, 1995.

Timm et al., "Fluorescent *In Situ* Hybridization En Suspension (FISHES) Using Digoxigenin-qLabeled Probes and Flow Cytometry," *Biotechniques* vol. 12, No. 3: 362-367, 1992.

Trask et al., "Fluorescence in situ hybridization to interphase cell nuclei in suspension allows flow cytometric analysis of chromosome content and microscopic analysis of nuclear organization," *Human Genetics* 78:251-259, 1988.

Tucker et al., "Extended depth of field and aberration control for inexpensive digital microscope systems" *Optics Express* vol. 4, No. 11: 467-474, May 24, 1999.

van Dekken et al., "Flow Cytometric Quantification of Human Chromosome Specific Repetitive DNA Sequences by Single and Bicolor Fluorescent In Situ Hybridization to Lymphocyte Interphase Nuclei," *Cytometry* 11: 153-164, 1990.

van den Berg et al., "Detection of Y Chromosome by *In situ* Hybridization in Combination with Membrane Antigens by Two-Color Immunofluorescence," *Laboratory Investigation* vol. 64, No. 5: 623-628, 1991.

Wang et al., "A Novel Apoptosis Research Method With Imaging-Combined Flow Cytometer and HITC OR IR-125 Staining," *Cytometry (Clinical Cytometry)* 50: 267-274, 2002.

Weber-Matthieson et al., "Rapid immunophenotypic characterization of chromosomally aberrant cells by the new FICTION method," *Cytogenetics Cell Genetics* 63: 123-125, 1993.

Weber-Matthieson et al., "Simultaneous Fluorescence Immunophenotyping and Interphase Cytogenetics: A Contribution to the Characterization of Tumor Cells," *Journal of Histochemistry and Cytochemistry* vol. 40, No. 2: 171-175, 1992.

Wietzorrek et al., "A New Multiparameter Flow Cytometer: Optical and Electrical Cell Analysis in Combination With Video Microscopy in Flow," *Cytometry* 35: 291-301, 1999.

Wyrobek et al., "Smokers produce more aneuploid sperm than non-smokers," *The American Society of Human Genetics*, 45th Annual Meeting, A131: 737, Oct. 24-28, 1995.

Wyrobek et al., "Detection of Sex Chromosomal Aneuploidies X-X, Y-Y, and X-Y, in Human Sperm Using Two-Chromosome Fluorescence In Situ Hybridization," *American Journal of Medical Genetics* 53: 1-7, 1994.

Wyrobek et al., "Fluorescence In Situ Hybridization to Y Chromosomes in Decondensed Human Sperm Nuclei," *Molecular Reproduction and Development* 27: 200-208, 1990.

Oberholzer et al., "Methods in quantitative image analysis." *Histochem Cell Biol*, vol. 105: 333-355, 1996.

Amann et al., "Fluorescent-Oligonucleotide Probing of Whole Cells for Determinative, Phylogenetic, and Environmental Studies in Microbiology," *Journal of Bacteriology* vol. 172, No. 2: 762-770, Feb. 1990.

Arkesteijn et al., "Chromosome Specific DNA Hybridization in Suspension for Flow Cytometric Detection of Chimerism in Bone Marrow Transplantation and Leukemia," *Cytometry* 19: 353-360, Apr. 1995.

Bains et al., "Flow Cytometric Quantitation of Sequence-Specific mRNA in Hemopoietic Cell Suspension by Primer-Induced *in Situ* (PRINS) Fluorescent Nucleotide Labeling," *Experimental Cell Research* 208: 321-326, Sep. 1993.

Barren III et al., "Method for Identifying Prostate Cells in Semen Using Flow Cytometry," *The Prostate* 36: 181-188, 1998.

Bauman et al., "Flow Cytometric Detection of Ribosomal RNA in Suspended Cells by Fluorescent In Situ Hybridization," *Cytometry* 9: 517-524, 1988.

Baumgartner et al., "Automated Evaluation of Frequencies of Aneuploid Sperm by Laser-Scanning Cytometry (LSC)," *Cytometry* 44: 156-160, 2001.

Ben-Eliezer et al., "All-optical extended depth of field imaging system," *Journal of Optics A: Pure and Applied Optics* 5: S164-S169, 2003.

Biggs et al., "Acceleration of iterative image restoration algorithms" *Applied Optics* vol. 36, No. 8: 1766-1775, Mar. 10, 1997.

Boyle et al., "Isolation and Initial Characterization of a Large Repeat Sequence Element Specific to Mouse Chromosome 8," *Genomics* vol. 12, No. 3: 517-525, 1992.

Callet-Bauchu et al., "Distribution of the cytogenetic abnormality +i(3)(q10) in persistent polyclonal B-cell lymphocytosis: a FICTION study in three cases," *British Journal of Haematology* 99: 531-536, Dec. 1997.

Ding et al., "Characterization and Quantitation of NF-κB Nuclear Translocation Induced by Interleukin-1 and Tumor Necrosis Factor-α," *The Journal of Biological Chemistry* vol. 273, No. 44: 28897-28905, Oct. 30, 1998.

Disteche et al., "Isolation and characterization of two repetitive DNA fragments located near the centromere of the mouse X chromosome," *Cytogenetics and Cell Genetics* 39: 262-268, 1985.

Dragowska et al., "Measurement of DNA repeat sequence by flow cytometry," *Cytometry* Supplement 7: 51, Oct. 1994.

Engvall, Eva. "Enzyme Immunoassay ELISA and EMIT," *Methods in Enzymology* vol. 70, Part A: 419-439, 1980.

Fernandez-Lago et al., "Fluorescent Whole-Cell Hybridization with 16S rRNA-Targeted Oligonucleotide Probes To Identify *Brucella* spp. by Flow Cytometry," *Journal of Clinical Microbiology* vol. 38, No. 7: 2768-2771, Jul. 2000.

George et al., "Extended depth of field using a logarithmic asphere" *Journal of Optics A: Pure and Applied Optics* 5: S157-S163, 2003.

George et al., "Distinguishing Modes of Cell Death Using the ImageStream® Multispectral Imaging Flow Cytometer," *Cytometry Part A* 59A: 237-245, 2004.

George et al., "Quantitative measurement of nuclear translocation events using similarity analysis of multispectral cellular images obtained in flow," *Journal of Immunological Methods* 311: 117-129, 2006.

Gordy et al., "Visualization of Antigen Presentation by Actin-Mediated Targeting of Glycolipid-Enriched Membrane Domains to the Immune Synapse of B cell APCs." *Journal of Immunology* vol. 172, No. 4: 2030-2038, Feb. 15, 2004.

\* cited by examiner

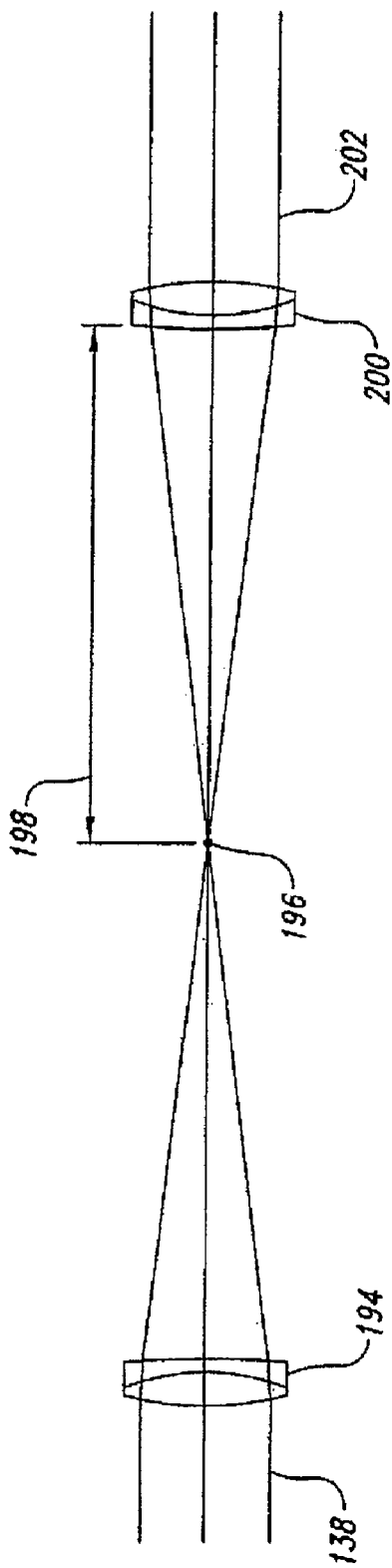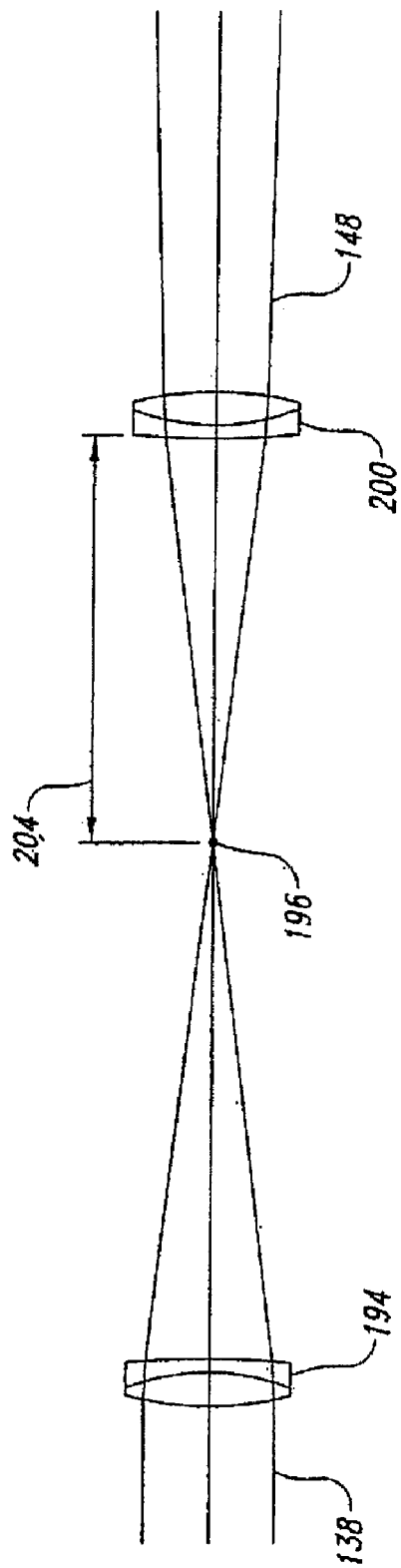

SYSTEM AND METHOD FOR HIGH NUMERIC APERTURE IMAGING SYSTEMS

RELATED APPLICATIONS

This application is a divisional application based on prior copending patent application Ser. No. 11/338,477, filed on Jan. 24, 2006, which is itself a divisional application based on prior patent application Ser. No. 09/977,076, filed on Oct. 12, 2001, which issued as U.S. Pat. No. 7,009,651 on Mar. 7, 2007, the benefit of the filing date of which is hereby claimed under 35 U.S.C. §120. Patent application Ser. No. 09/977,076, noted above, is also based on prior provisional application Ser. No. 60/240,125, filed on Oct. 12, 2000, the benefit of the filing date of which is hereby claimed under 35 U.S.C. §119(e).

BACKGROUND

The invention relates generally to imaging systems, and more particularly to systems and methods for high numeric aperture imaging involving low-light and high-resolution, such as used for microscopic imaging of biological samples or macroscopic imaging of astronomical samples.

SUMMARY

This application specifically incorporates by reference the disclosures and drawings of each patent application and issued patent identified above as a related application.

A system and method for high numeric aperture imaging systems includes aspects directed to a first beam splitter configured to substantially transmit part of received light as first transmitted light and to substantially reflect part of received light as first reflected light. Further aspects include a defocus system configured to modify optical power of substantially one of the following: the first transmitted light and the first reflected light, and to transmit the same as first transmitted defocused light. Additional aspects include a reflector configured to reflect one of the following: the first reflected light and the first transmitted defocused light. Further aspects include a second beam splitter configured to substantially transmit part of one of the following: the first transmitted light as second transmitted light and the first transmitted defocused light as second transmitted defocused light and configured to substantially reflect part of one of the following: the first transmitted defocused light as second reflected defocused light and the first reflected light as second reflected light.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 11-12 are schematics illustrating an alternative implementation of a component of the imaging system, as shown in FIGS. 2-3 and FIGS. 6-9.

DESCRIPTION

Figure 1:
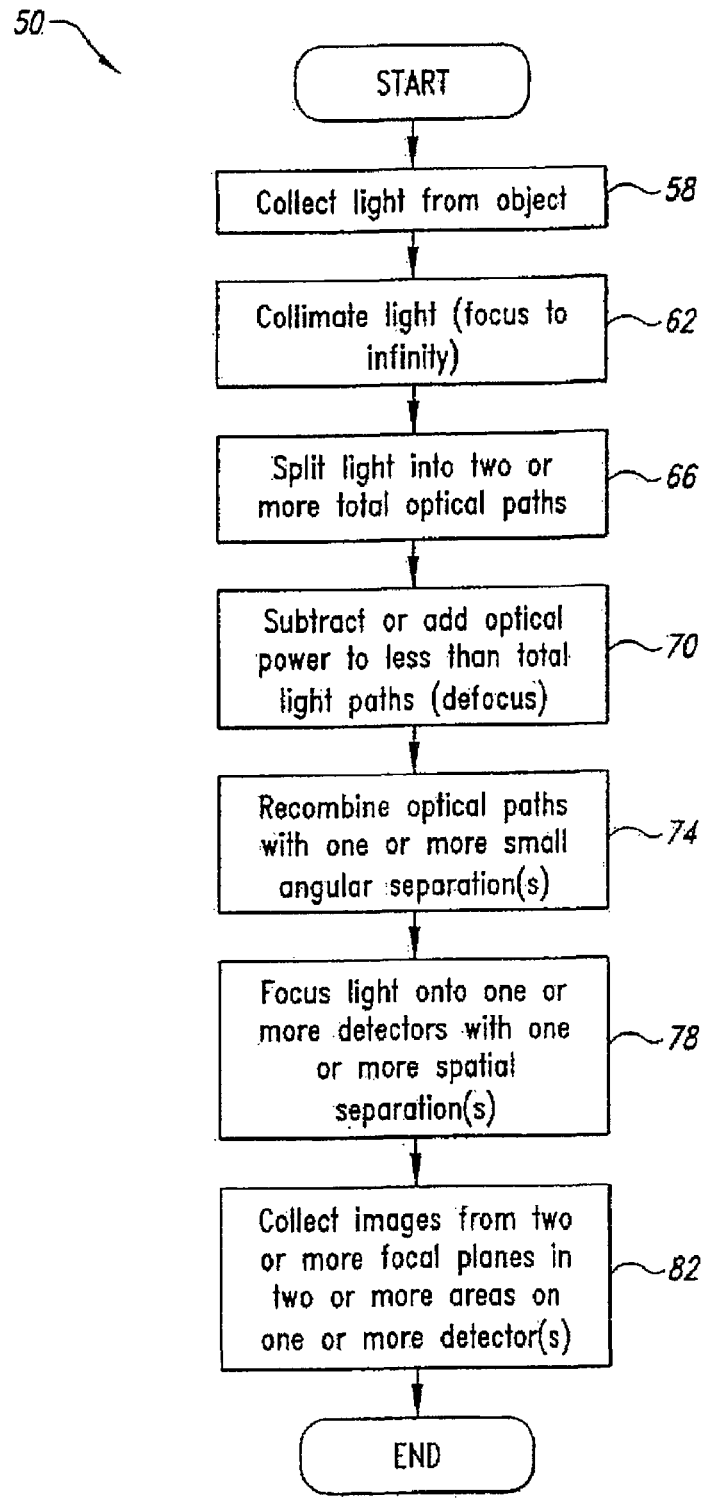
FIG. 1 is a flowchart illustrating a method for augmenting depth of field at a target object for low-light, high-resolution imaging.

Figures and Disclosed Embodiments are not Limiting

Exemplary embodiments are illustrated in referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

Described herein are systems and methods for achieving and maintaining focus of target objects subject to low-light, high-resolution imaging. In general, light either reflecting, scattering or emanating from a target object is collected and split into two or more light components. The optical power levels of some, but not all the light components are then modified such that when the light components are recombined with an angular separation to form an image, each of the light components have differently positioned image planes where an object point of the target object is imaged.

For each image plane pair, a detector is such that each detector receives focused images from two object planes at the target object associated with the image plane pair of the detector to increase depth of field and focusing capability. In some implementations, focus is actively maintained though computer automated positioning of components. Other implementations actively maintain focus with a feedback arrangement integral to a two-dimensional imaging system.

In the following description, numerous specific details are provided to understand embodiments of the invention. One skilled in the relevant art, however, will recognize that the invention can be practiced without one or more of these specific details, or with other equivalent elements and components, etc. In other instances, well-known components and elements are not shown, or not described in detail, to avoid obscuring aspects of the invention or for brevity. In other instances, the invention may still be practiced if steps of the various methods described could be combined, added to, removed, or rearranged.

A method 50 used by implementations of low-light, high-resolution imaging systems is illustrated in FIG. 1. The method 50 first collects light from a target object, such as emanating, scattered, reflected, and/or refracted light (step 58). The collected light is then collimated by focusing to infinity (step 62). The collimated light is then split into a collective total consisting of two or more optical paths (steps 66). Optical power is then added or subtracted from the light in a chosen one or more, but not all, of the optical paths of the collective total to defocus the light in the chosen one or more optical paths (step 70). Light in the collective total of optical paths is then recombined wherein light of the one or more chosen optical paths has one or more small angular separations with respect to light of other optical paths of the collective total (step 74).

The recombined light is then focused on one or more detectors resulting in one or more spatial separations of the imaged target object based upon two or more image planes at the imaged target object associated with two or more object planes at the target object (step 78). Images of the imaged target object associated with the two or more image planes are then collected by the one or more detectors for analysis (step 82) and the method 50 ends to be ready for further imaging of other target objects. As an example, if two optical paths make up the collective total, then optical power of only one of the paths is altered so that there is a spatial separation between two images resulting from the two light paths on a detector. For an image plane defined by the detector, there are two conjugate object planes separated along the optical axis of the imaging system. Optical power of the one path is altered to control the axial separation between the object planes so that the depth of field provided by the first image just overlaps the depth of field provided by the second image to extend the total depth of field of the imaging system.

Figure 2:
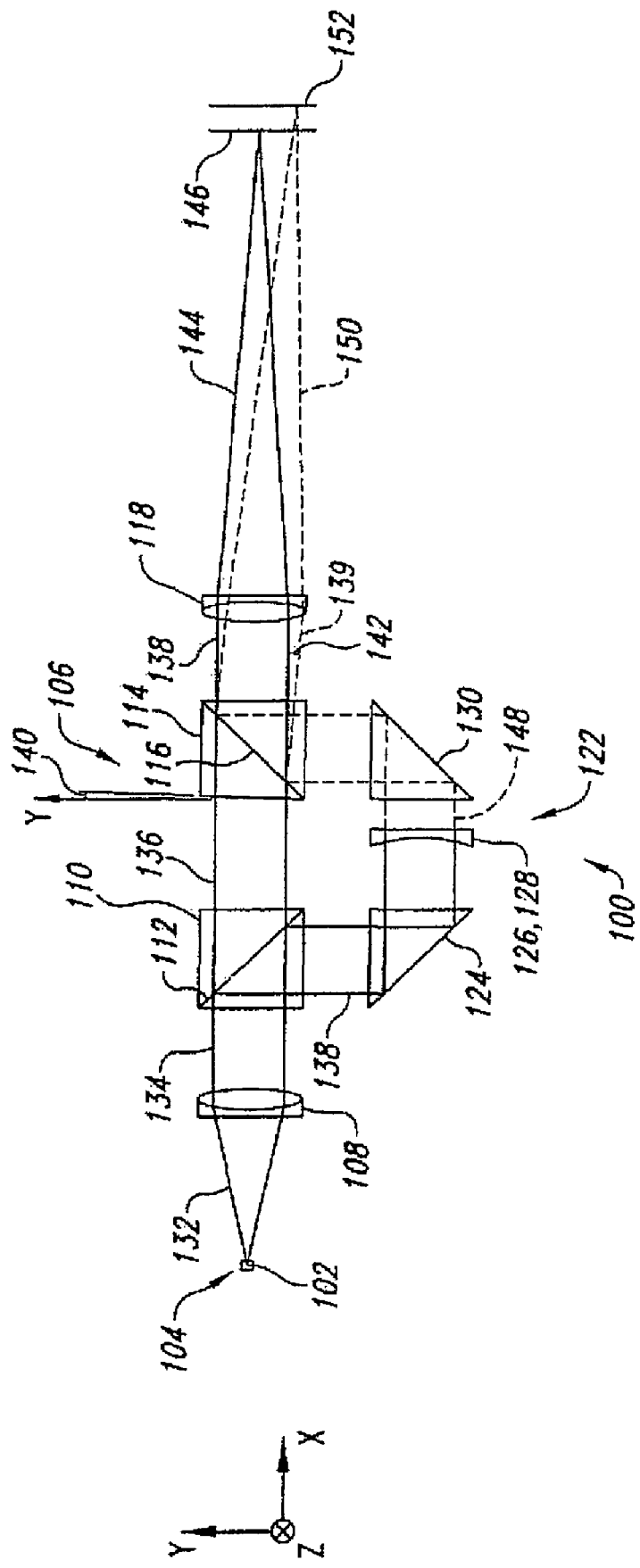
FIGS. 2-3 are schematics illustrating an imaging system for low-light, high-resolution imaging.

An implementation of an imaging system 100 as shown in FIG. 2 is configured to produce multi-focal plane images of a target object 102, such as biological cells or other small particles, being transported by a fluid flow, in the direction of the z-axis of FIG. 2, through a flow cell cuvette 104. The imaging system 100 has an unaltered optical path 106 with a collection lens 108, an amplitude beam splitter 110 with a beam splitter optical coating 112, an amplitude beam splitter 114 with a beam splitter optical coating 116, an imaging lens 118, and a first detector 120 (shown in FIG. 3). The imaging system 100 also has a defocus optical path 122 with a first reflector 124, a defocus system 126 being a negative lens 128 in the implementation shown, and a second reflector 130 and sharing the collection lens 108, the beam splitter optical coating 112, the amplitude beam splitter 114, the imaging lens 118, and the first detector 120 with the unaltered optical path 106. The target object 102, being the subject of imaging by the imaging system 100 and found in the flow cell cuvette 104, emits, reflects, scatters, or refracts object light 132 to be received, collected, and passed by the collection lens 108 as collected light 134 being collimated light having generally parallel light rays being focused approximately at infinity. The collected light 134 enters the amplitude beam splitter 110, which splits the collected light into two optical paths having a first transmitted light 136 and a first reflected light 138, respectively, in accordance with the beam splitter optical coating 112 on the amplitude beam splitter.

The first transmitted light 136 is left unaltered and passes through the amplitude beam splitter 114 in accordance with the beam splitter optical coating 116 as second transmitted first transmitted light (2T1T light) 138. The amplitude beam splitter 114 is oriented slightly by a mechanical angle 104 with respect to the y-axis such that the second reflected defocused light (2R defocused light) is oriented at an optical angle of separation 142 with respect to both the x-axis and the 2T1T light 138. The 2T1T light 138 is then focused by the imaging lens 118 as imaged 2T1T light 144, which converges to focus at 2T1T image plane 146. The first reflected light 138 reflected by the beam splitter optical coating 112 is redirected by the first reflector 124 to pass through the defocus system 126 thereby producing defocused first reflected light (defocused 1R light) 148, being decollimated light having optical power modified by the defocus system. The defocused 1R light 148 is then redirected by the second reflector 130 to pass through the amplitude beam splitter 114 to be reflected in accordance with the beam splitter optical coating 116. The 2R defocused light is brought to focus by the imaging lens 118 as imaged 2R defocused light 150, at 2R defocused image plane 152.

Figure 3:
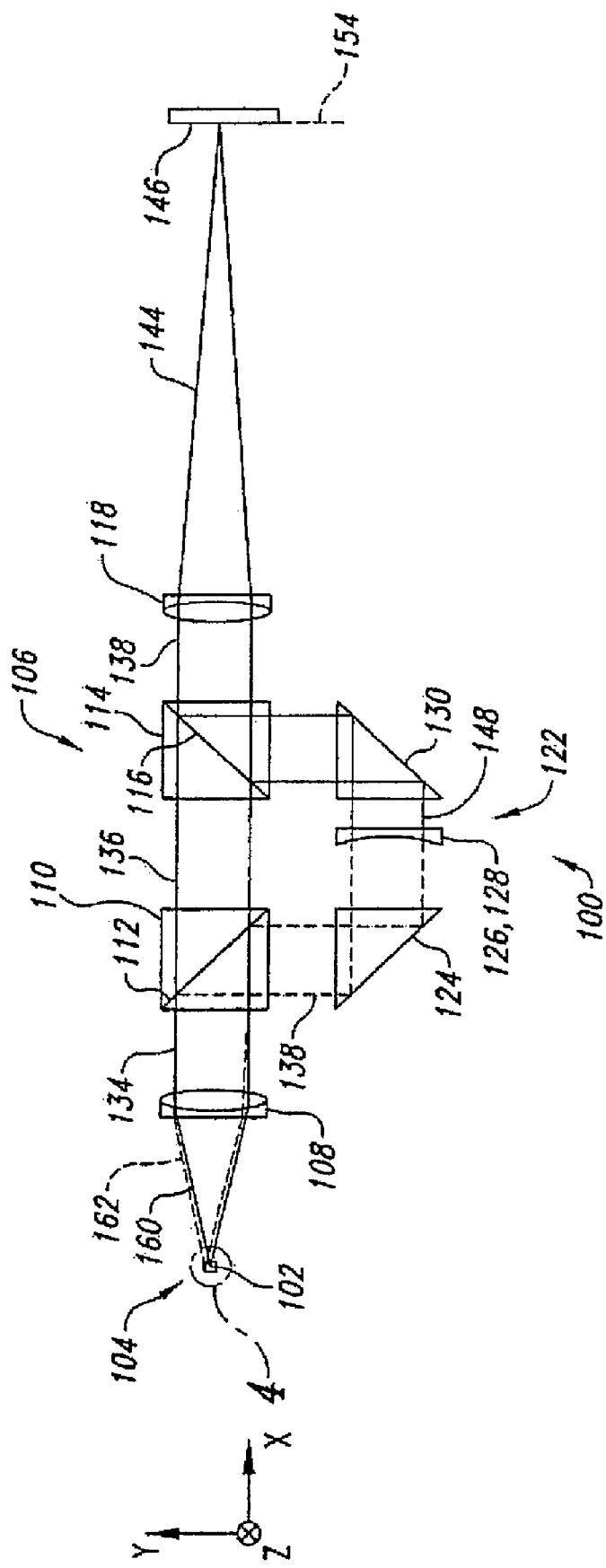
Figure 4:
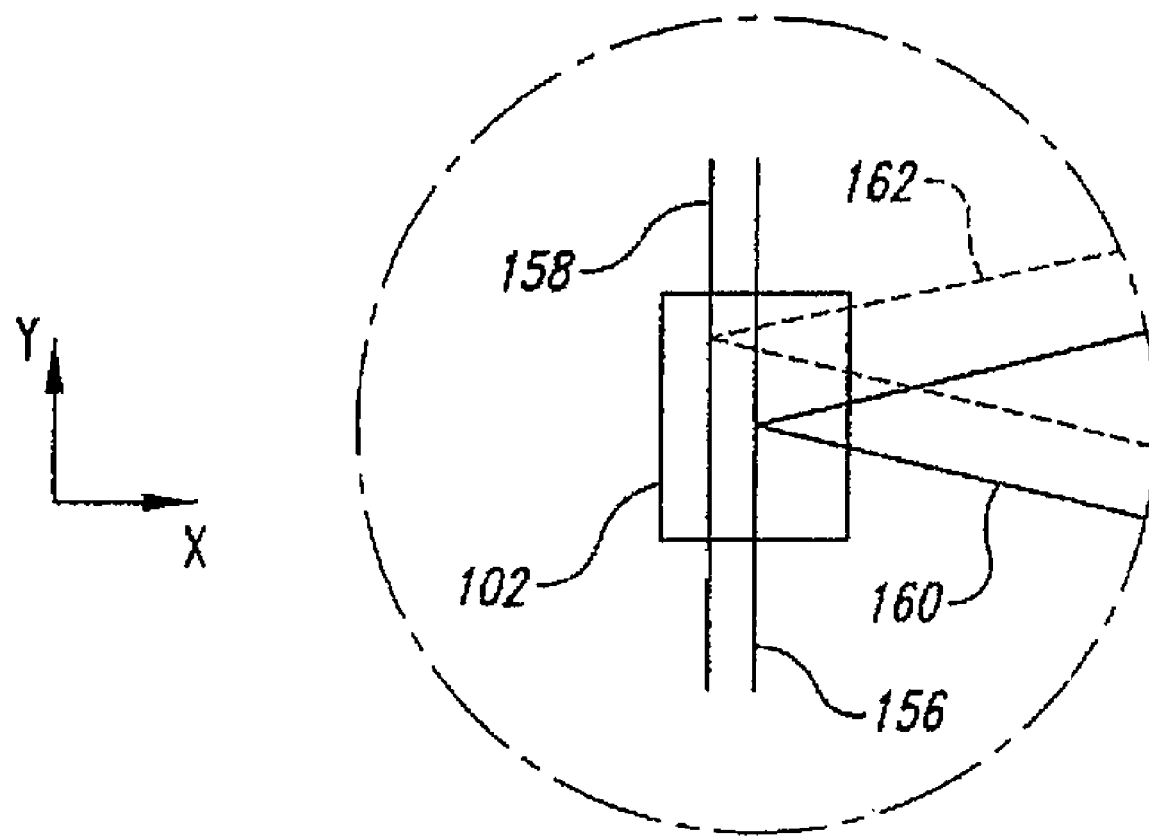
FIGS. 4-5 are schematics illustrating object planes associated with the imaging system, as shown in FIGS. 2-3.
Figure 5:
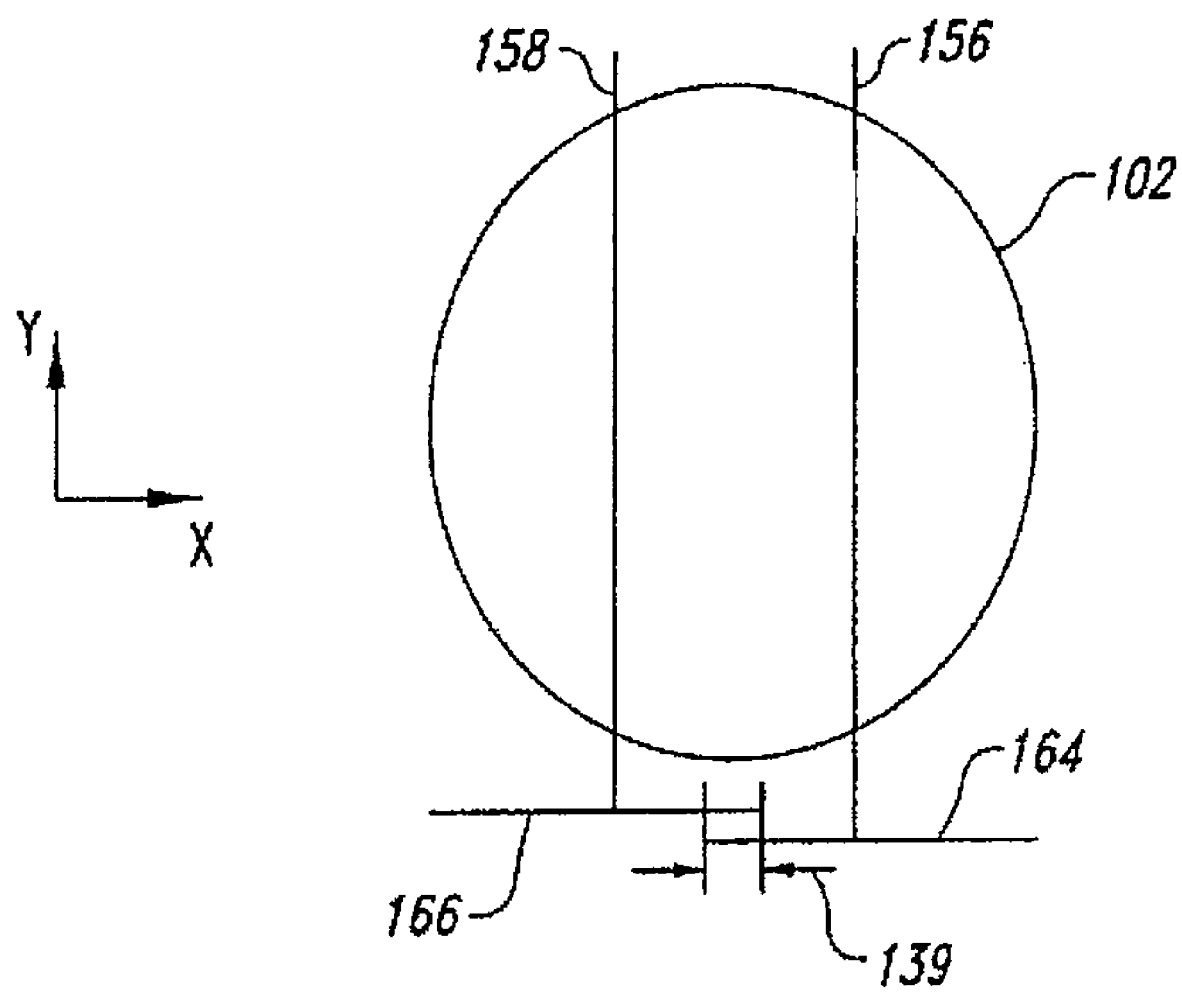
Figure 6:
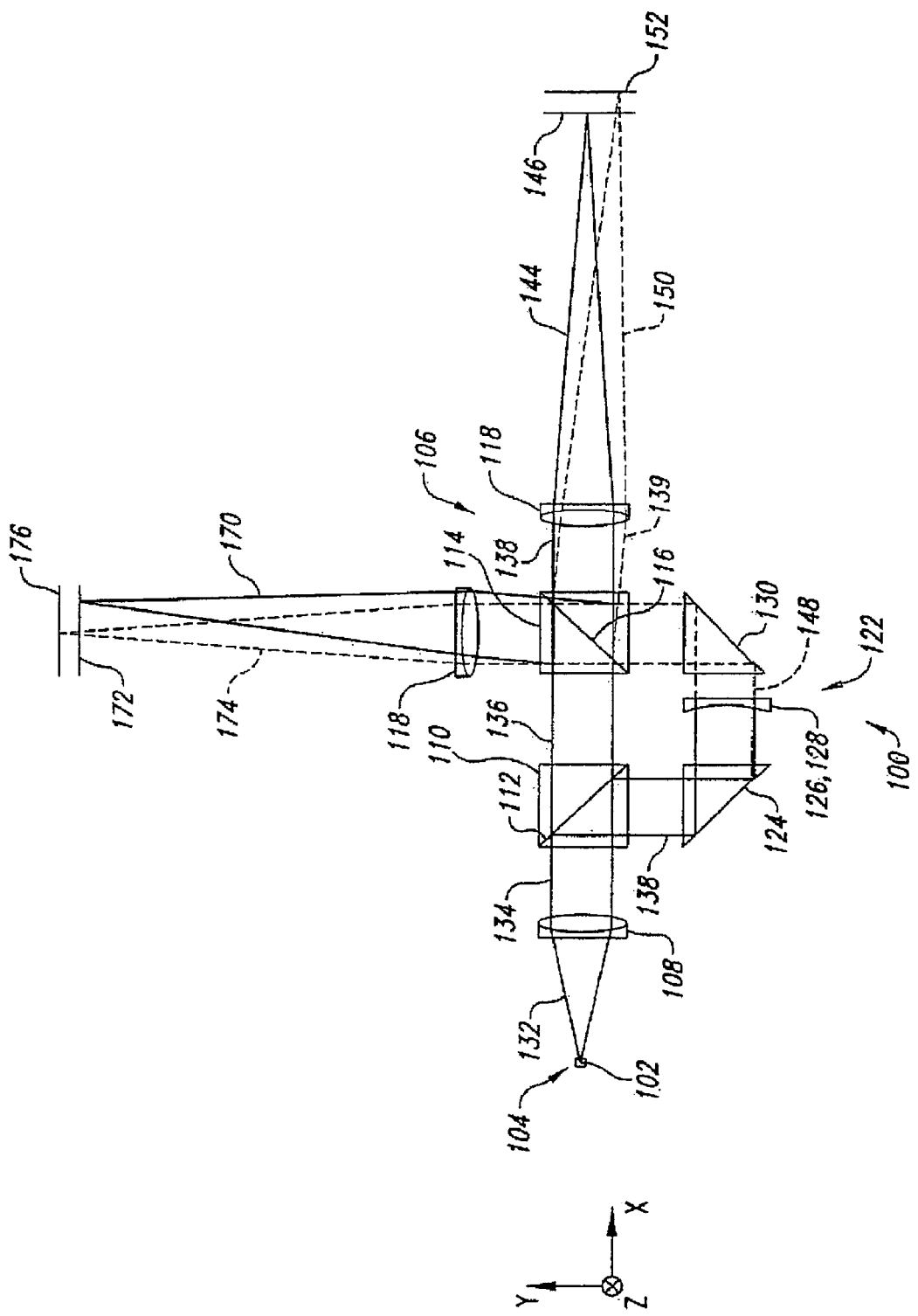
FIGS. 6-9 are schematics illustrating alternative implementations of the imaging system, as shown in FIGS. 2-3.
Figure 7:
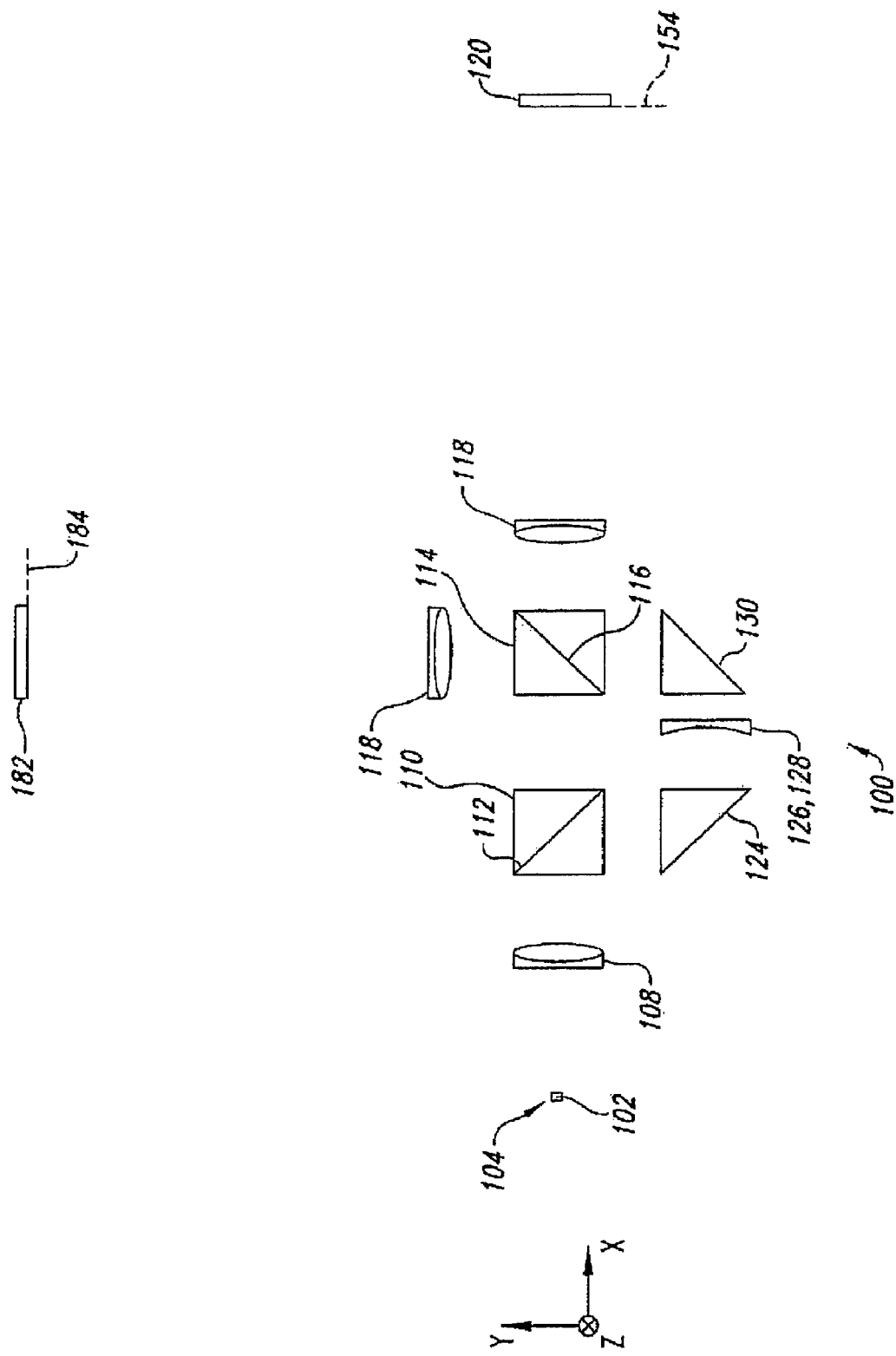
Figure 8:
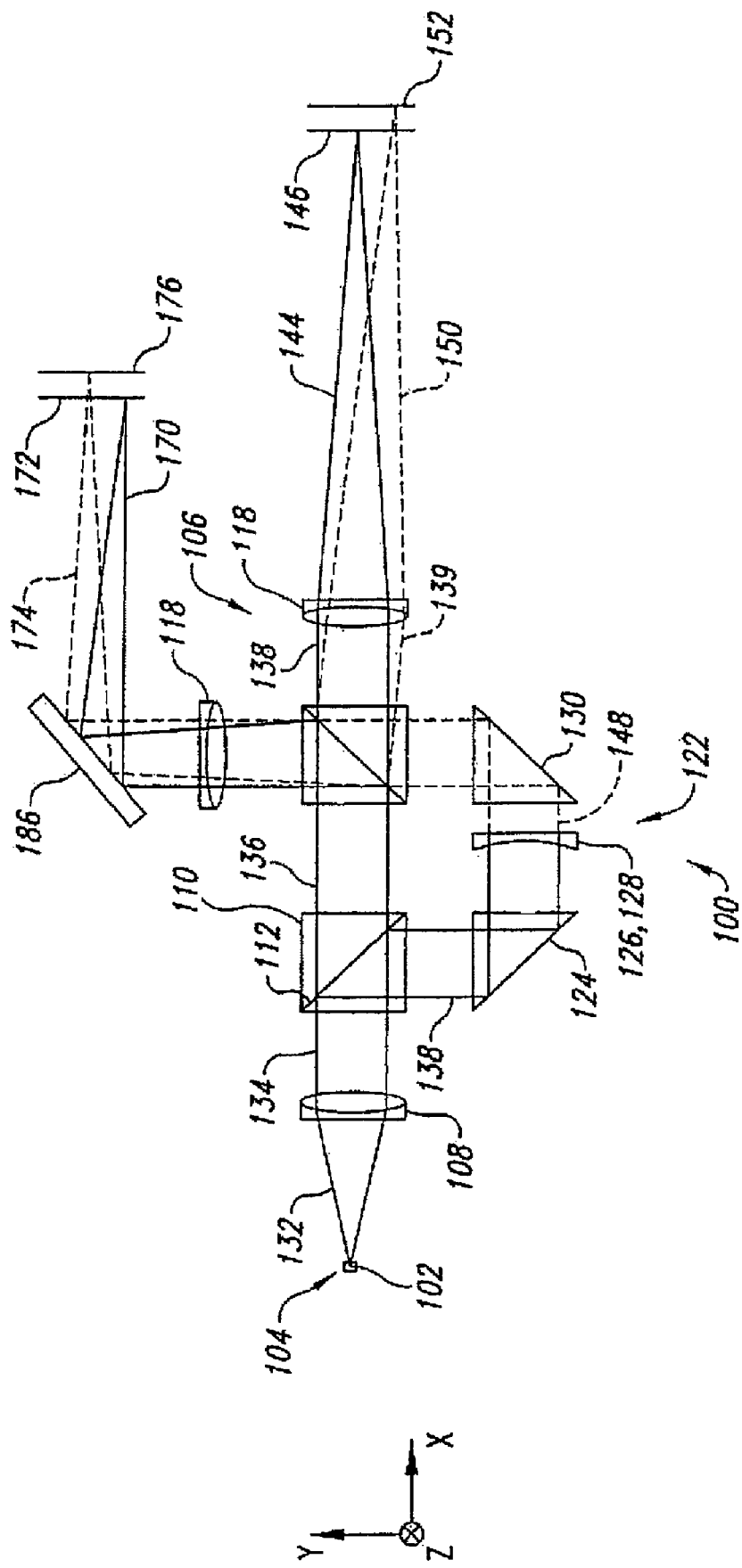
Figure 9:
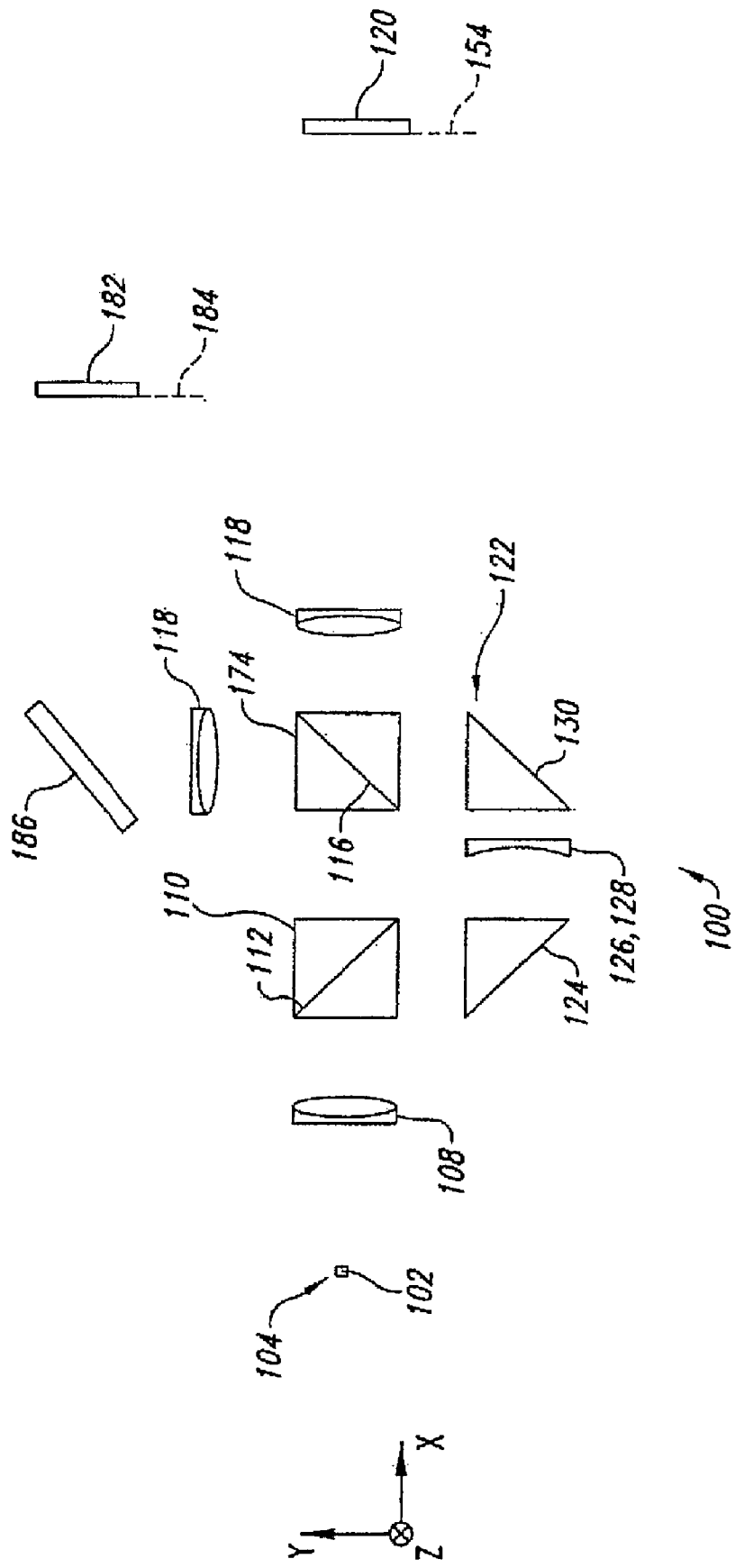

The amount of defocus introduced by the defocus system 126 results in the 2T1T image plane 146 and 2R defocused image plane 152 being spatially separated from one another along the x-axis such that their depths of focus overlap. As shown in FIG. 3, the first detector 120 is positioned with respect to a first detector image plane 154 and uses this overlap of depths of focus of the 2T1T image plane 146 and the 2R defocused image plane 152 to effectively increase the overall depth of focus of the imaging system 100 for the first detector. The imaging system 100 provides, for the first detector 120 in the first detector image plane 154, two conjugate 2T1T object planes 156 and 2R defocused object plane 158 associated with an unaltered object light 160 and a defocus object light 162, respectively, as shown in FIGS. 3-5. As shown in FIG. 5, the 2T1T object plane 156 has a 2T1T object field depth 164 and the 2R defocused object plane 158 has a 2R defocused object field depth 166, which have a first object field depth overlap 168. In other implementations the first object field depth overlap 168 may not exist for other tailoring of the depth of focus.

Implementations include the beam splitter optical coating 112 and the beam splitter optical coating 116 being an amplitude beam splitter type with transmittance and reflectance being nominally equal. The optical component of the amplitude beam splitter 110 and the amplitude beam splitter 114 and their respective beam splitter optical coating 112 and beam splitter optical coating 116 may have the coatings bonded between two prism elements. Alternative implementations use plate or pellicle versions of the amplitude beam splitter 110 and the amplitude beam splitter 114 with their respective beam splitter optical coating 112 and beam splitter optical coating 116 being deposited on one surface. In some implementations, the first reflector 124 and the second reflector 130 are prisms, as illustrated, having total internal reflection from uncoated surfaces. Other implementations of the first reflector 124 and the second reflector 130 use reflective metallic or dielectric optical coatings deposited on surfaces including, but not limited to, a mirror surface of a plane mirror.

It is important to control intensities of the imaged 2T1T light 144 and the imaged 2R defocused light 150, so that, typically, the image intensities are substantially equal at the first detector 120. Intensity control can be achieved in a number of ways. Depending upon the relative optical path efficiencies, such as the optical efficiency of the unaltered optical path 106 versus the optical efficiency of the defocus optical path 122, it may be desirable to employ other than an equal transmittance/reflectance ratio for the beam splitter optical coating 112 or the beam splitter optical coating 116. For example, if the additional optical elements in the defocus optical path 122 were to result in more absorption loss relative to the unaltered optical path 106, it would be beneficial to reflect more light at the beam splitter optical coating 112 and transmit less light to the unaltered optical path to balance the light intensity in the imaged 2T1T light 144 and the imaged 2R defocused light 150. Commonly available transmittance/reflectance split ratios for commercially available beam splitter coatings include 50/50, 60/40, 40/60, 30/70, and 70/30. Other implementations using other split ratios for light intensity control are readily achievable with customized optical coatings known in the art.

In addition to the choice of beam splitter coating, such as choice of the beam splitter optical coating 112 or the beam splitter optical coating 116, light intensity can be controlled by placement of neutral density (ND) filters in the unaltered optical path 106 or the defocus optical path 122. In some implementations, reflective or absorptive type filters are used to reduce intensity in the unaltered optical path 106 or the defocus optical path 122 to match that of the other. For instance, a single filter of the appropriate density value is used in some implementations to correct the mismatch while a variable density filter component such as a stepped ND filter or linear wedge neutral density filter is used in other implementations where optical density of the coating varies linearly with position as needed. Implementations using a variable density filter take advantage of its convenient light intensity adjustment and single design approach to compensate for variation in component efficiencies in a manufacturing environment.

Figure 10:
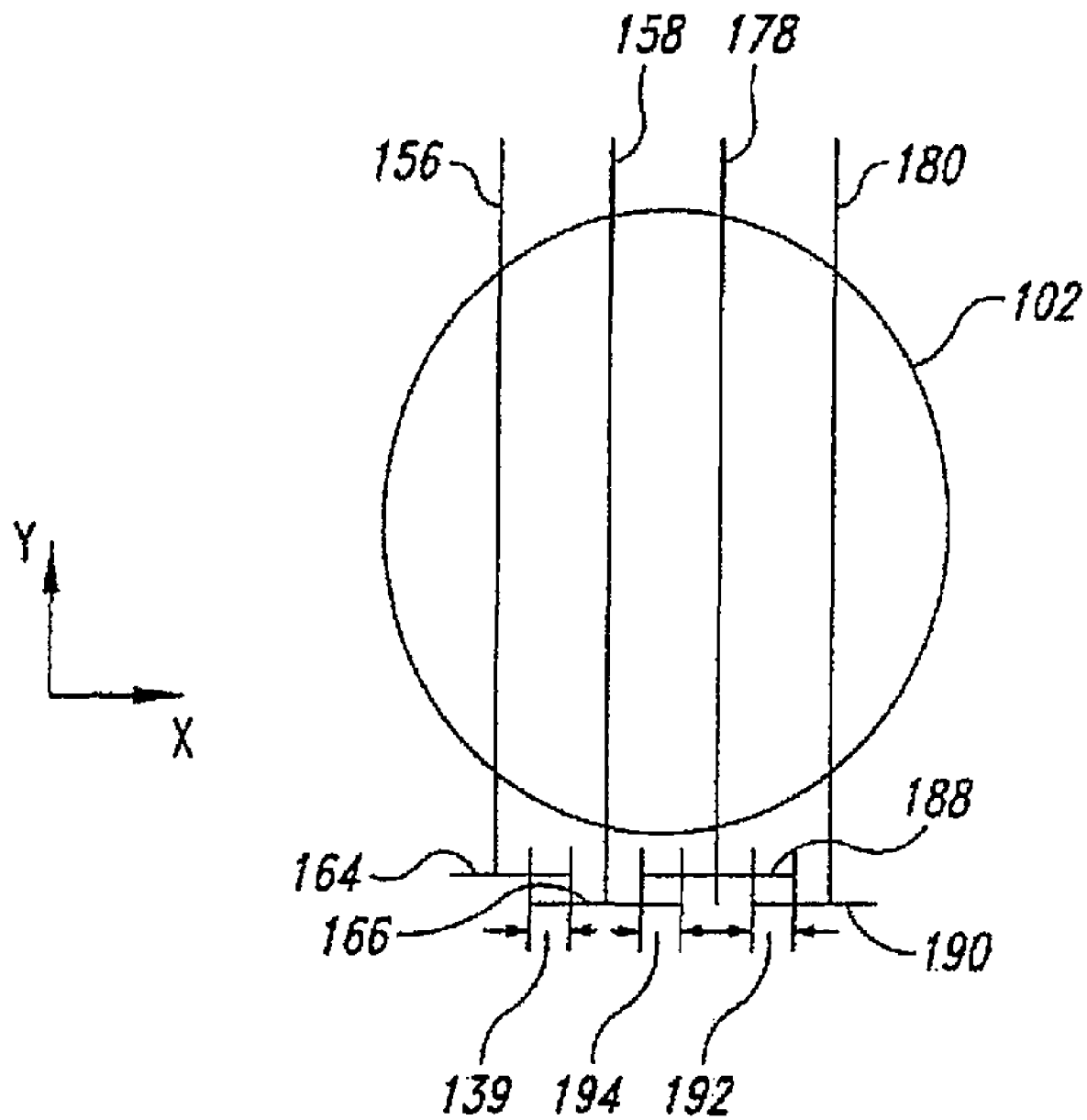
FIG. 10 is a schematic illustrating object planes associated with the imaging systems, as shown in FIGS. 6-9.

In alternative implementations of the imaging system 100 illustrated in FIGS. 6-9, a second of the imaging lens 118 is used to focus that portion of the first transmitted light 136 reflected by the beam splitter optical coating 116 of the amplitude beam splitter 114 into an imaged 2R1T light 170 on the 2R1T image plane 172. The second imaging lens 118 also focuses that portion of the defocused 1R light 148 transmitted by the beam splitter optical coating 116 of the amplitude beam splitter 114 into imaged 2T defocused light 174 onto the 2T defocused image plane 176. The 2R1T image plane 172 and the 2T defocused image plane 176 have a corresponding 2R1T object plane 178 and a 2T defocused image plane 180, respectively. The implementations also have a second detector 182 along a second detector image plane 184 to receive the 2R1T image plane 172 and the 2R defocused focus cell images 232. One implementation also uses an additional reflector 186 to redirect the 2R1T image plane 172 and the 2T defocused image plane 176. As illustrated in FIG. 10, the 2R1T object plane 178 has a 2R1T object field depth 188 and the 2T defocused image plane 180 has a 2T defocused object field depth 190, which share a second object field depth overlap 192. The 2R defocused object field depth 166 and the 2R1T object field depth 188 also share a third object field depth overlap 194.

As shown, the defocus system 126 can be implemented as the negative lens 128. In other implementations, the defocus system 126 can be a positive lens element or a compound optical system configured to decollimate inputted collimated light. Implementations include lens elements being ground and polished or molded, being glass or plastic, being reflective or refractive, and having spherical or aspherical surfaces. Implementations using compound optical systems may include both transmissive and reflective optics. An exemplary compound optical system implementation of the defocus system 126 is illustrated in FIGS. 11 and 12 where the first reflected light 138, as collimated light, enters a first positive lens 194 and is brought to focus at an intermediate focal point 196. As shown in FIG. 11, a focused lens spacing 198 between the intermediate focal point 196 and a second positive lens 200 is set to the focal length of the second positive lens such that a collimated light 202 leaves the defocus system 126.

The performance of the exemplary implementation illustrated in FIG. 11 could be duplicated by any number of lens combinations conventionally known. In order to modify the optical power of the first reflected light 138, either optical power is added or subtracted from the first reflected light by the defocus system 126. As shown in FIG. 12, negative optical power is introduced into the first reflected light 138 by shortening the intermediate focal point 196 to a defocused lens spacing 204 being less than the focal length of the second positive lens 200. The shorter length of the defocused lens spacing 204 results in a divergence of light exiting the second positive lens 200 of the defocus system 126 as defocused 1R light 148. If positive power is introduced to the first reflected light 138, the length of the defocused lens spacing 204 is made greater than the focused lens spacing 198 resulting in a convergence of light exiting the second positive lens 200 of the defocus system 126.

Figure 13:
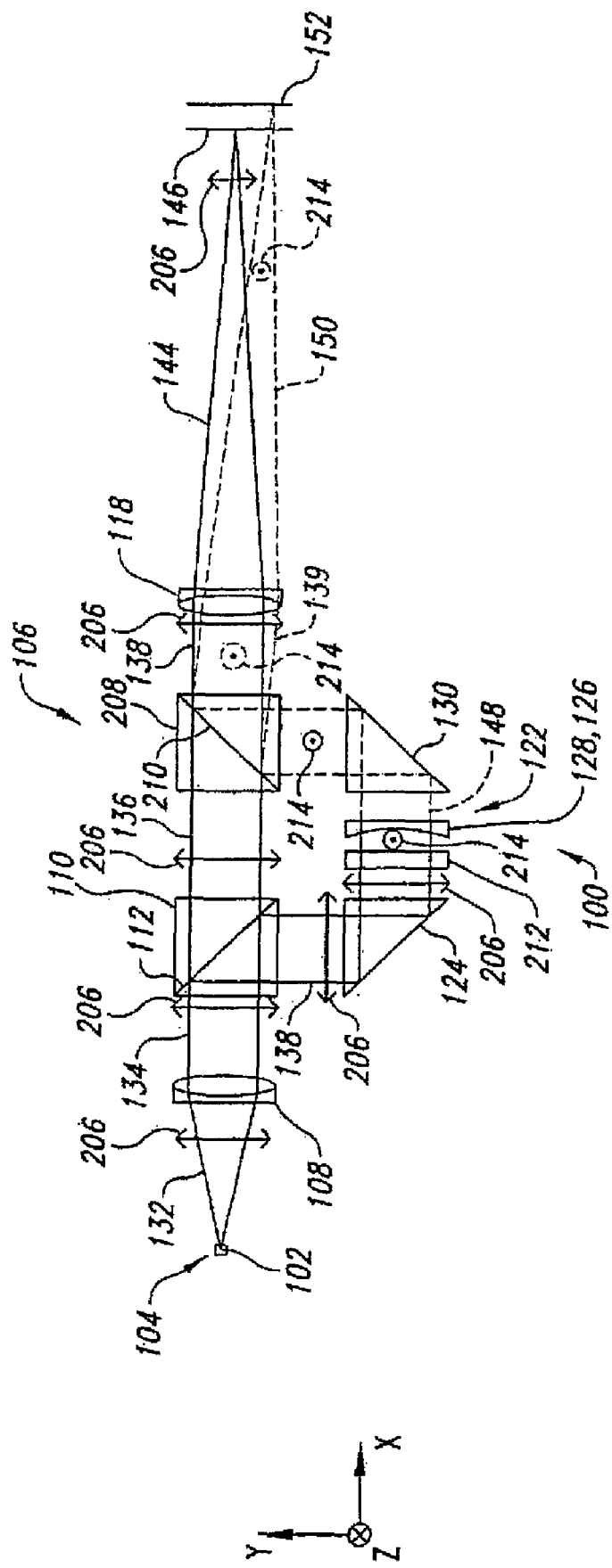
FIGS. 13-14 are schematics illustrating an alternative implementation of the imaging system, as shown in FIGS. 2-3 and FIGS. 6-9.
Figure 14:
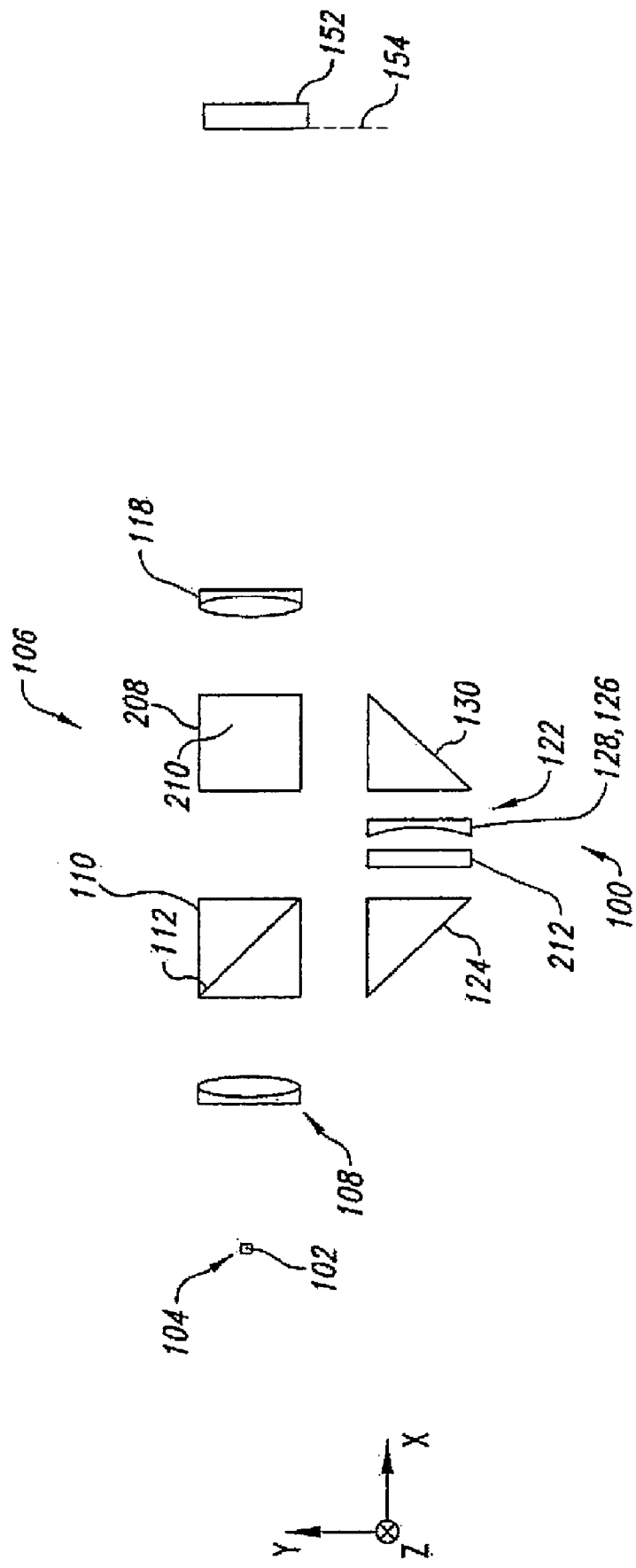

An alternative implementation of the imaging system 100 uses a version of the object light 132 being linearly polarized having a first polarization state vector 206 oriented in the x-y plane, as illustrated in FIG. 13. The collection lens 108, the beam splitter optical coating 112, and the first reflector 124 act upon the object light 132, the collected light 134, and the first reflected light 138, respectively, without affecting the orientation of the first polarization state vector 206. In this implementation, the imaging system 100 uses a polarization beam splitter 208 having a polarization beam splitter optical coating 210 being oriented in the polarization beam splitter such that the first transmitted light 136, with its particularly oriented first polarization state vector 206, passes substantially completely through the polarization beam splitter 208 as the 2T1T light 138 due to the orientation of the first polarization state vector. After leaving the first reflector 124, the first reflected light 138 passes through an optical retardation plate 212 thereby altering the first polarization state vector 206 to a second polarization state vector 214 being oriented in the x-z plane, as illustrated in FIG. 13. Subsequently, the defocused 1R light 148, having the second polarization state vector 214, is substantially completely reflected off of the polarization beam splitter 208 of the polarization beam splitter optical coating 210 as the 2R defocused light due to the orientation of the second polarization state vector. As a result of the polarization effect associated with the polarization beam splitter 208, both the 2T1T light 138 and the 2R defocused light are substantially brighter compared to other implementations of the imaging system 100 not relying upon the polarization effect. When compared with other implementations, optical efficiency is approximately doubled by utilizing the polarization effect although there is some absorption loss associated with the optical retardation plate 212.

Figure 15:
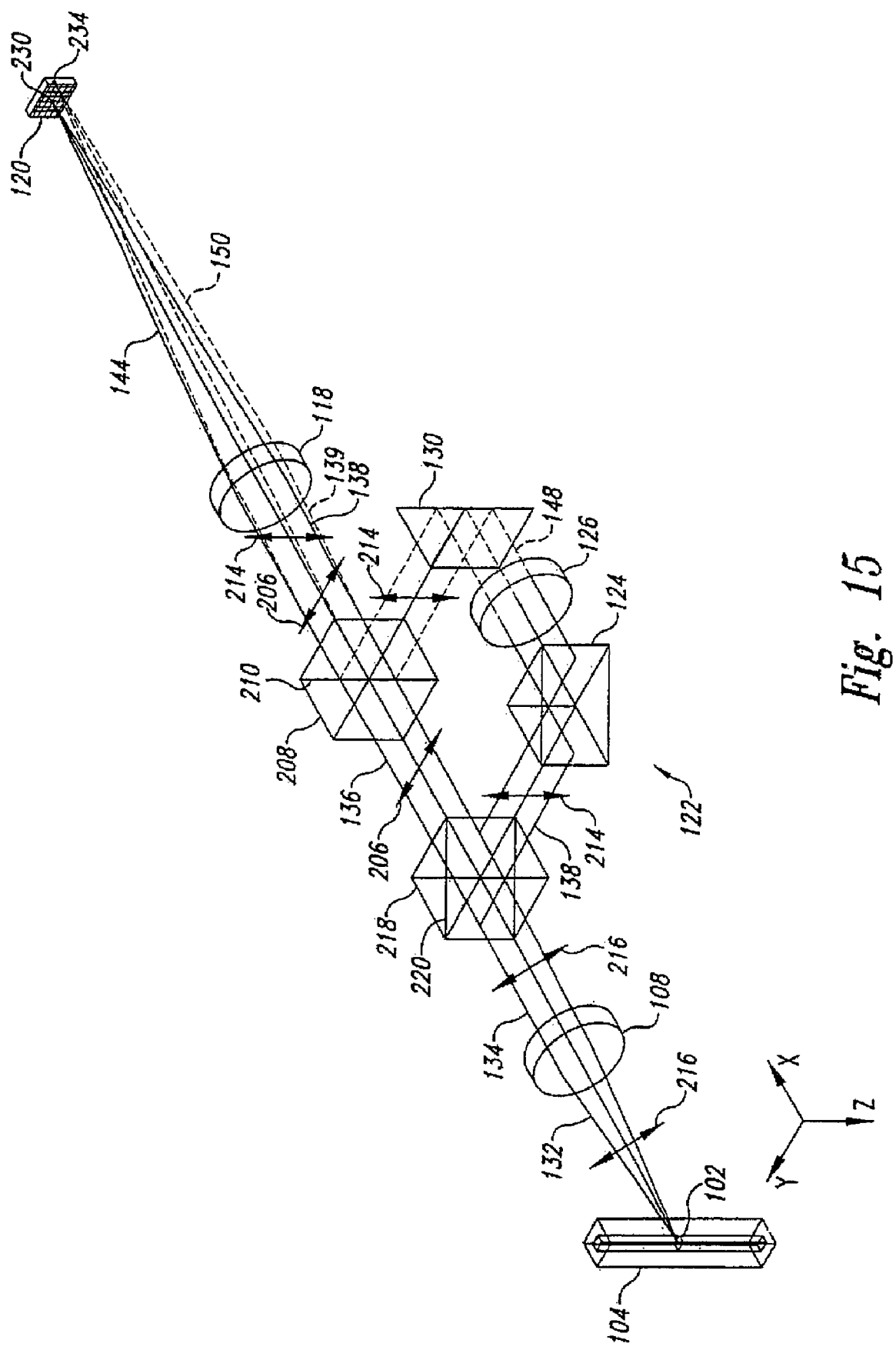
FIG. 15 is a schematic illustrating an alternative implementation of the imaging system, as shown in FIGS. 2-3, FIGS. 6-9, and FIGS. 13-14.

An alternative implementation of the imaging system 100 uses a polarized and un-polarized versions of the object light 132. The polarized version of the object light 132 has a third polarization state vector 216 oriented in the y-z plane and approximately 45 degrees relative to both the y-axis and the z-axis, as illustrated in FIG. 15. The collection lens 108 passes the object light 132 as the collected light 134 without affecting polarization. A polarization beam splitter 218 having a polarization beam splitter optical coating 220 receives both polarized and un-polarized versions of the collected light 134 and splits the collected light into a polarized version of first transmitted light 136 having the first polarization state vector 206 oriented along the y-axis plane and a polarized version of the first reflected light 138 having the second polarization state vector 214 oriented along the z-axis.

The first reflector 124, and the second reflector 130 do not substantially alter the polarization of the first reflected light 138 with the second polarization state vector. The polarization beam splitter optical coating 210 of the polarization beam splitter 208 is oriented such that the first transmitted light 136 with the first polarization state vector 206 passes substantially completely through the polarization beam splitter optical coating of the polarization beam splitter as 2T1T light 138 also with the first polarization state vector and the defocused 1R light 148 with the second polarization state vector 214 is substantially completely reflected off of the polarization beam splitter optical coating of the polarization beam splitter as 2R defocused light also with the second polarization state vector. As a result, an approximate doubling of optical efficiency is achieved, as compared with other implementations, without additional expense and absorption loss associated with use of the optical retardation plate 212.

Figure 16:
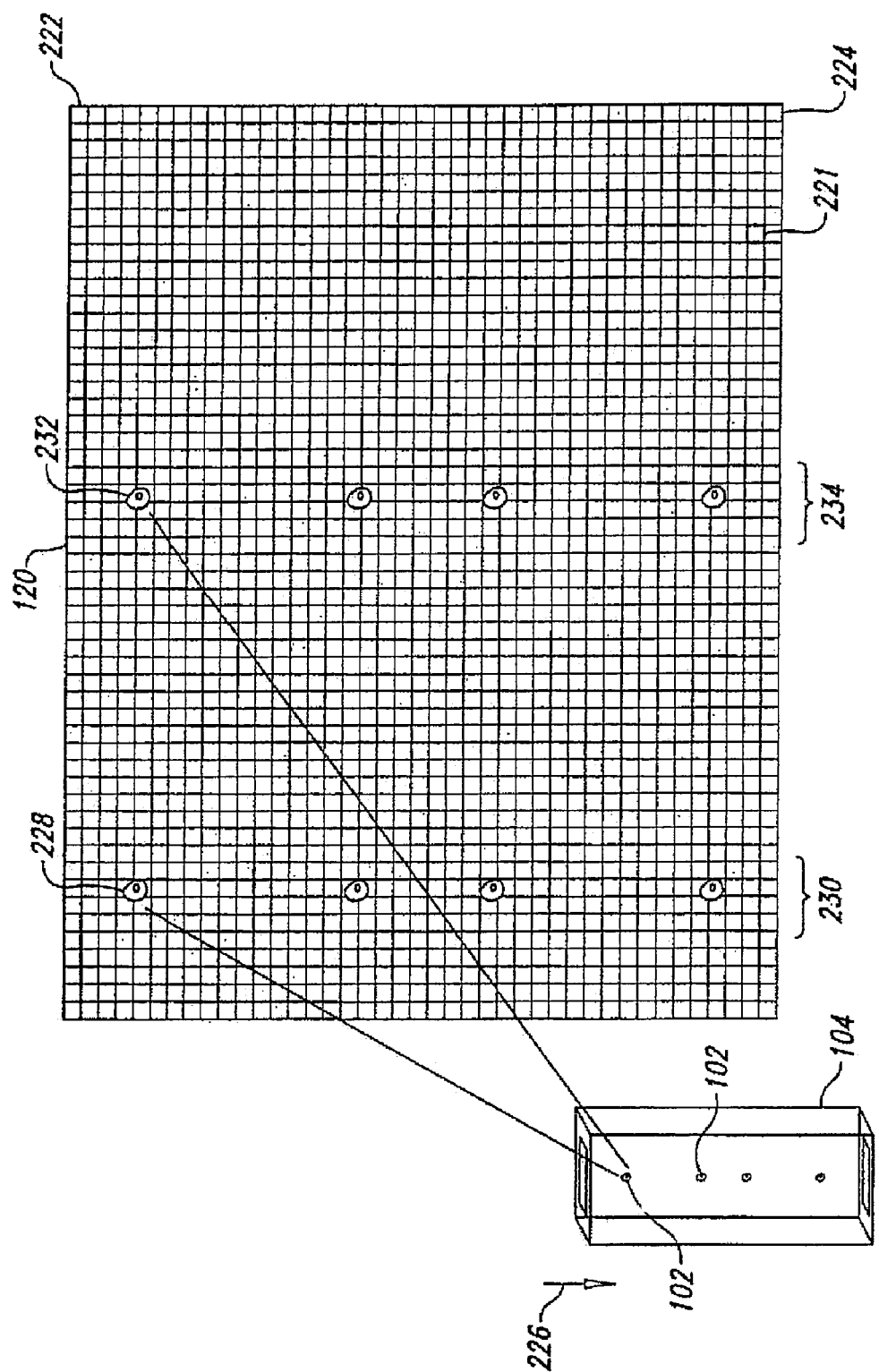
FIG. 16 is a schematic illustrating an exemplary set of images on a detector of the imaging system, as shown in FIGS. 2-3, FIGS. 6-9, and FIGS. 13-14.

An implementation of the first detector 120, composed of picture elements such as detector pixels arranged in detector row 222 and detector columns 224, is illustrated in FIG. 16. Typically, such an implementation of the first detector 120 would utilize time delay integration (TDI). Cells or other objects as the target object 102 are entrained in a fluid stream to be imaged on the first detector 120 as they flow in a fluid flow direction 226 through the flow cell cuvette 104. Sets of 2T1T focus cell images 228 in a 2T1T focus area 230 and 2R defocused focus cell images 232 in a 2R defocused focus area 234 are imaged on the first detector 120 along the detector columns 224. The 2T1T focus area 230 and the 2R defocused focus area 234 are spatially separated from one another by a suitable number of the detector pixels to avoid image overlap. For instance, in typical implementations for imaging cells having nominally 10 micron diameters, the 2T1T object field of view 164 is configured to be approximately 90 microns. Given an exemplary 10 pixel separation between the 2T1T focus area 230 and the 2R defocused focus area 234 and with an exemplary implementation of the first detector 120 having 13 micron sized pixels, a satisfactory channel separation would be 100 pixels or 1.3 mm. Furthermore, as an example, if the imaging system 100 were to have an overall magnification of 40×, and focal length of 200 mm for the imaging lens 118, the optical angle of separation 142 between the imaged 2T1T light 144 and the imaged 2R defocused light 150 would be approximately 6.5 milliradians. Consequently, in this example, the mechanical angle 104 for the amplitude beam splitter 114 would be approximately 3.25 milliradians.

Figure 17:
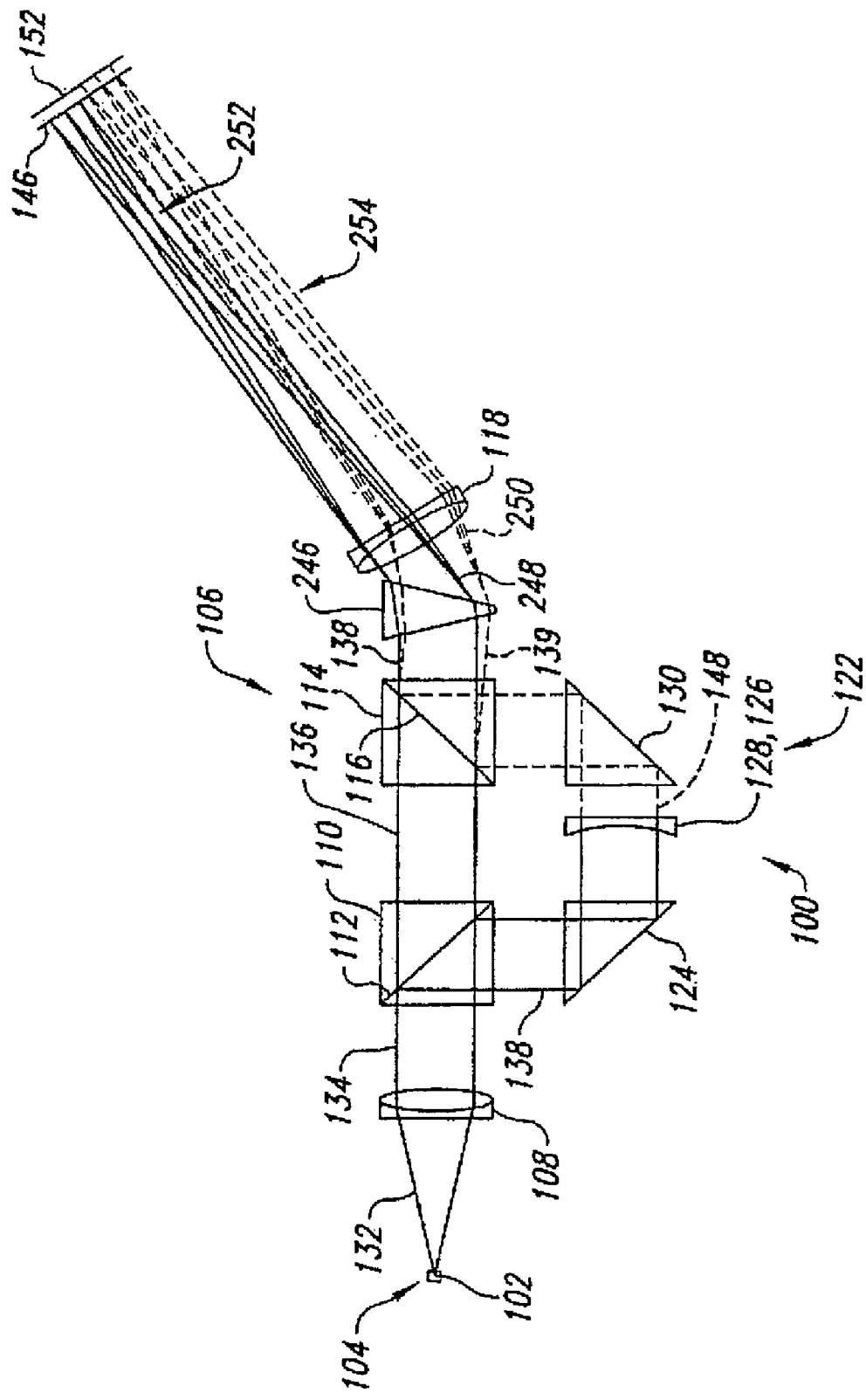
FIGS. 17-18 are schematics illustrating an alternative implementation of the imaging system, as shown in FIGS. 2-3, FIGS. 6-9, FIGS. 13-15.
Figure 18:
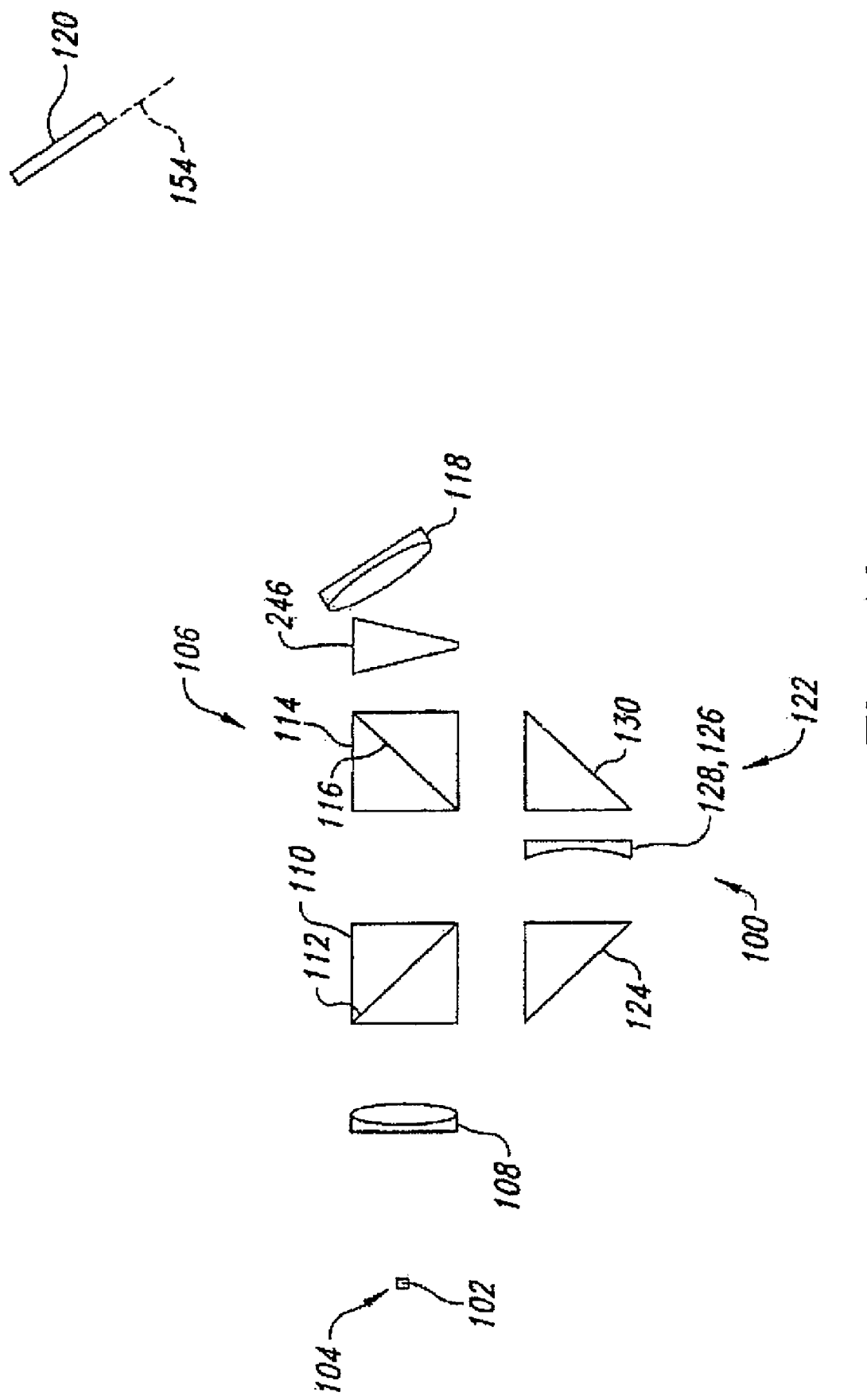
Figure 19:
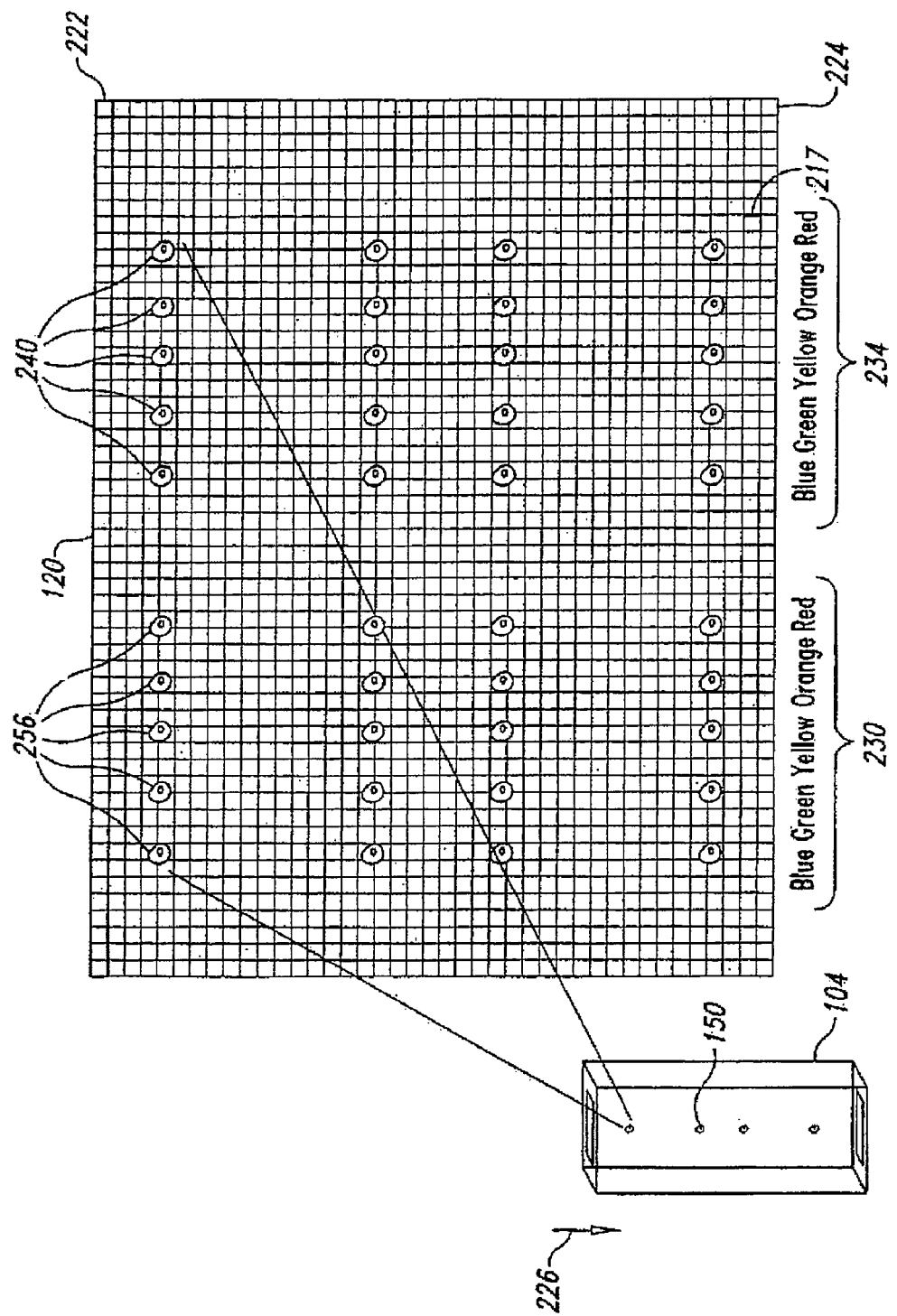
FIG. 19 is a schematic illustrating an exemplary set of images on a detector of the imaging system, as shown in FIGS. 17-18.

Another implementation of the imaging system 100, illustrated in FIGS. 17 and 18, uses a spectral dispersing element 246, such as a prism or diffraction grating, to spectrally disperse light from the amplitude beam splitter 114, shown in FIG. 17, or from the polarization beam splitter 208, not shown in FIG. 17, such as the 2T1T light 138 and the 2R defocused light to transmit spectrally dispersed 2T1T light 248 and spectrally dispersed 2R defocused light 250. The imaging lens 118 then receives the spectrally dispersed 2T1T light 248 and spectrally dispersed 2R defocused light 250 to transmit imaged, spectrally dispersed 2T1T light 252 and imaged, spectrally dispersed 2R defocused light 254, respectively, having the 2T1T image plane 146 and the 2R defocused image plane 152, with respect to a common point on target object 102, respectively. As illustrated in FIG. 19, the 2T1T focus area 230 and the 2R defocused focus area 234 have a spectrally dispersed band of images, 2T1T focus cell dispersed image set 256 and 2R defocused focus cell dispersed image set 258, respectively, for each occurrence of the target object 102. This spectral dispersion is useful for analysis of the target object 102.

Figure 20:
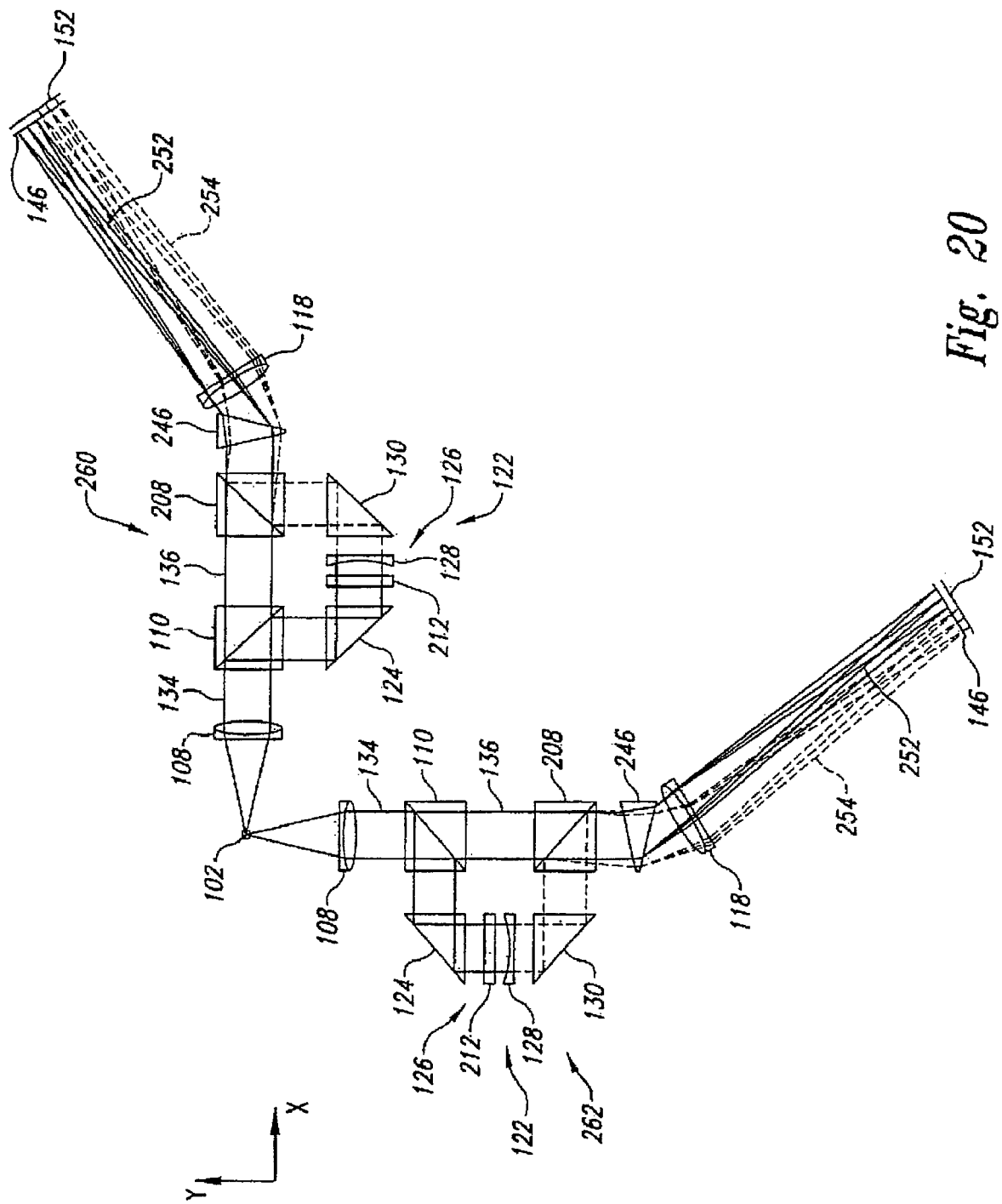
FIGS. 20-21 are schematics illustrating an alternative implementation of the imaging system, as shown in FIGS. 2-3, FIGS. 6-9, FIGS. 13-15, FIGS. 17-18, and FIGS. 20-21.
Figure 21:
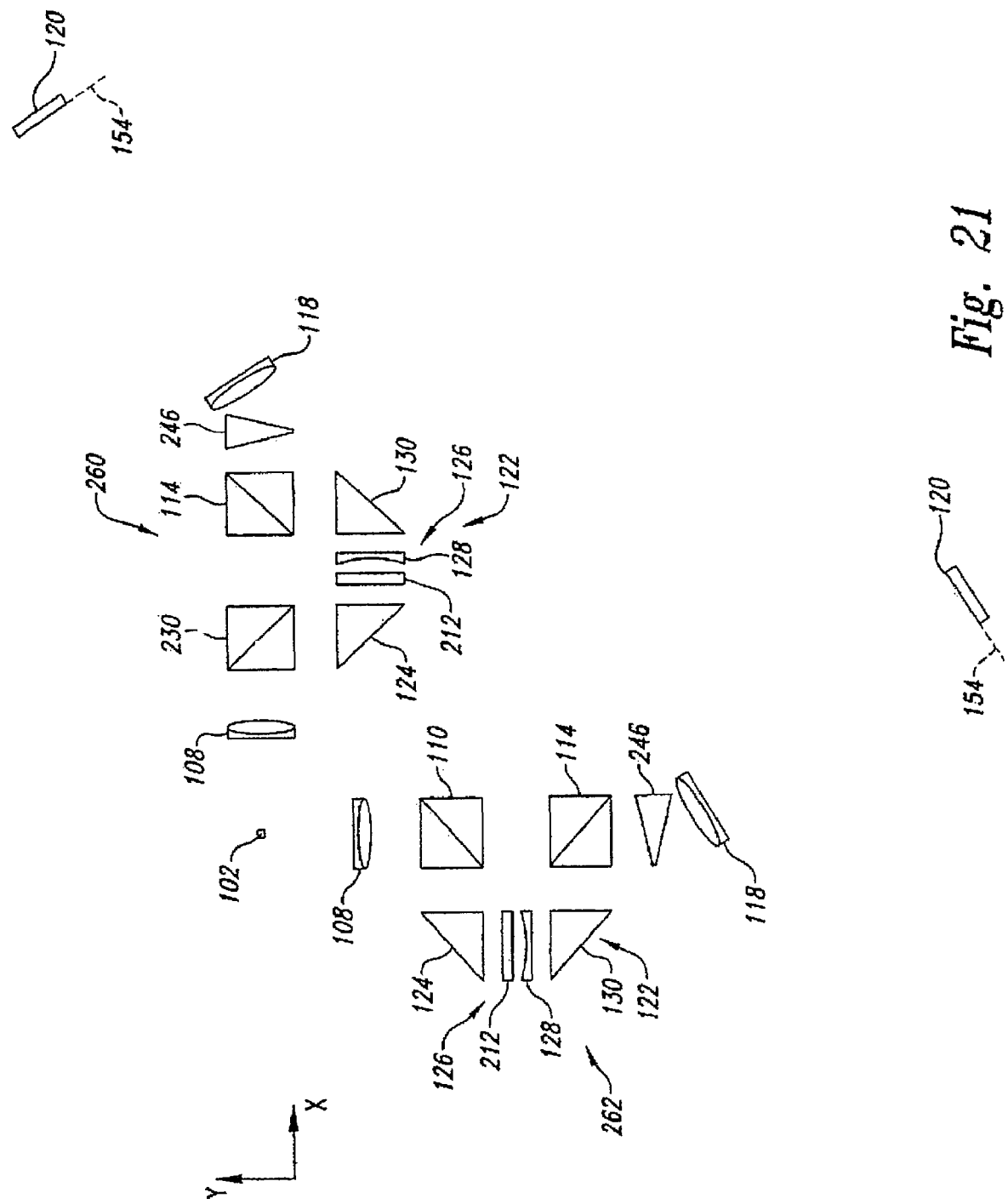

Another implementation of the imaging system 100, illustrated in FIG. 20, uses an x-axis imaging system 260 and a y-axis imaging system 262 to image the target object 102 bi-dimensionally from two different orientations, which is useful, for instance, to distinguish features that may otherwise overlap when viewed from a single orientation. The particular implementation illustrated in FIG. 20 utilizes polarization effects in conjunction with the optical retardation plate 212 and the polarization beam splitter 208 and spectral dispersion effects in conjunction with the spectral dispersing element 246. However, other implementations can use the x-axis imaging system 260 and the y-axis imaging system 262 with or without the polarization effects and the spectral dispersion effects.

Applications of bi-dimensional implementations of the imaging system 100 include analyzing multi-component objects in solution, such as cells containing FISH probes. Since FISH probes appear as point sources of light within the three-dimensional nucleus of a cell, in some cases, two or more FISH probes may appear in an overlapping relationship along the optical axis of the imaging system. Consequently, one or more FISH probes may obscure one or more other FISH probes to undermine attempts at determining the quantity of FISH probes contained within a cell. Determination of FISH probe quantity within a cell has tremendous utility such as in determining genetic abnormalities, (for example, trisomy 21, otherwise known as Down's syndrome).

By positioning the optical axes of the x-axis imaging system 260 and the y-axis imaging system 262 so that they are oriented with respect to one another by 90°, such as the optical axis of the x-axis imaging system being along the x-axis and the optical axis of the y-axis imaging system being along the y-axis, as shown in FIG. 20, it is possible to separately resolve image spots imaged from corresponding two or more FISH probe objects on at least one of the first detectors 120 of at least one of the x-axis imaging system and the y-axis imaging system. It has been found that if two or more FISH probes overlap in regard to the image produced on one of the first detectors 120, the two or more FISH probes can be separately resolved in the spectrally dispersed images produced on the other first detector.

This is in contrast to conventional approaches where single-orientation systems may address problems caused by image overlap due to defocus by panning through objects along the optical axis of the conventional systems to acquire multiple image planes in the object. These conventional approaches require significant amounts of time to collect multiple images and cannot readily be applied to objects, such as cells, in flow. The implementation of the imaging system 100 using two imaging sub-systems, the x-axis imaging system 260 and the y-axis imaging system 262, addresses image overlap problems, even while objects to be imaged are in motion, through its multi-object plane approach.

Figure 22:
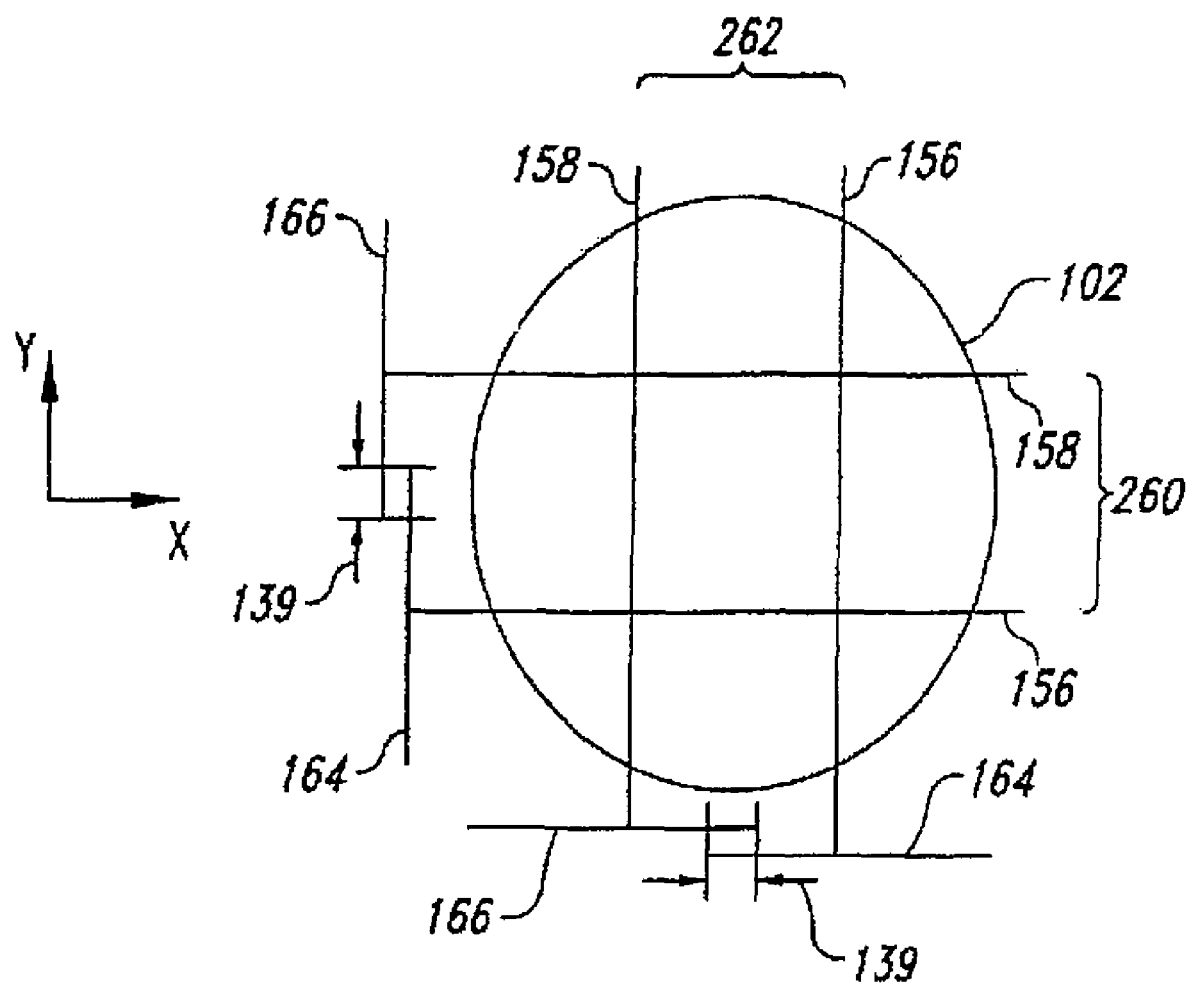
FIG. 22 is a schematic illustrating object planes associated with the imaging system, as shown in FIGS. 20-21.

Object planes associated with an orthogonal orientation of the optical axis of the x-axis imaging system 260 with respect to the y-axis imaging system 262 are illustrated in FIG. 22. As a result of the orthogonal orientation of the optical axis of the x-axis imaging system 260 with respect to the y-axis imaging system 262, the 2T1T object plane 156 and the 2R defocused object plane 158 of the x-axis imaging system are also orthogonal with respect to the 2T1T object plane and the 2R defocused object plane of the y-axis imaging system.

Figure 23:
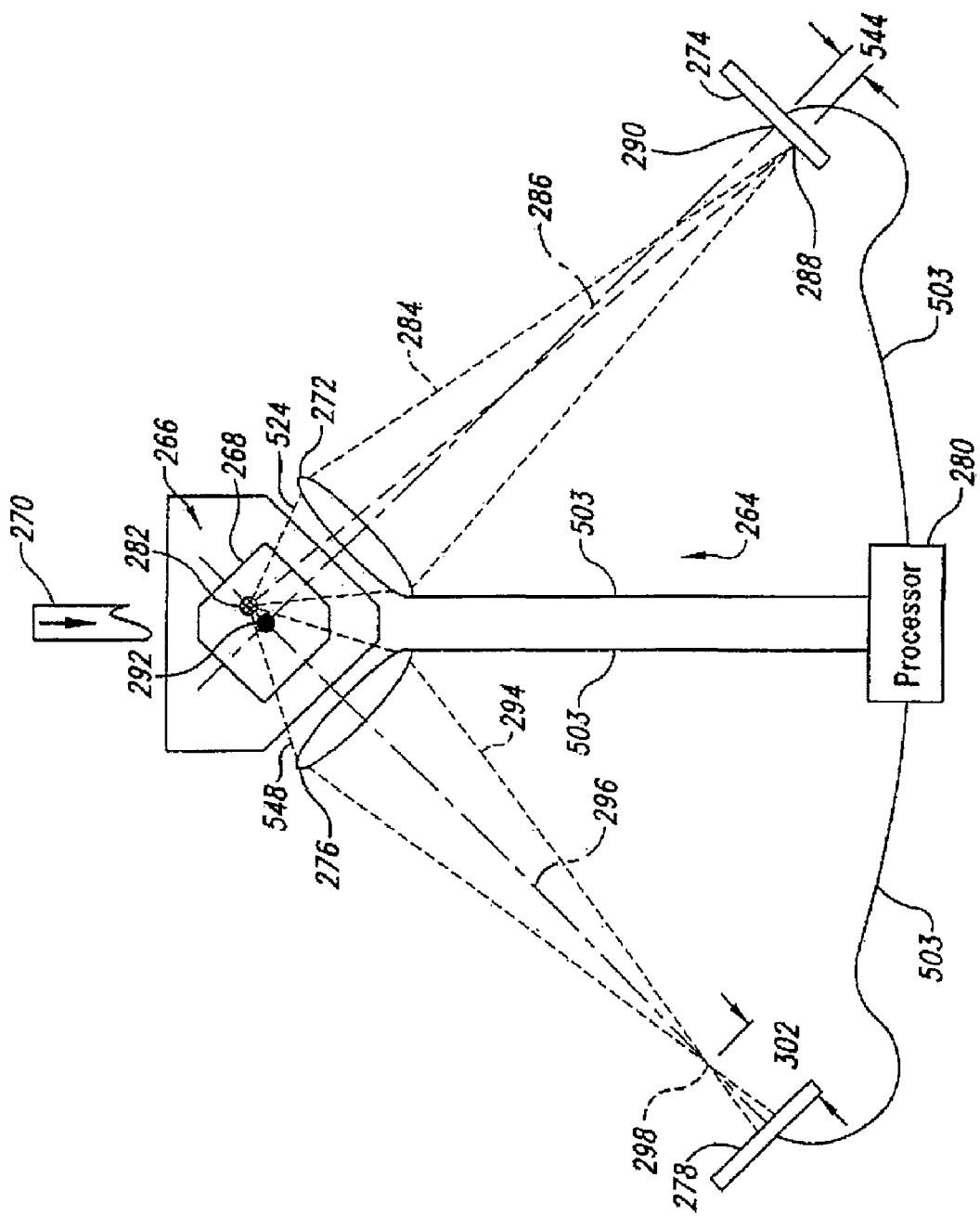
FIG. 23 is a schematic illustrating a two-dimensional imaging system using active focusing.

In an alternative implementation of the imaging system 100 as a bi-oriented imaging system 264, illustrated in FIG. 23, a focus feedback error is generated to dynamically acquire or maintain focus. The bi-oriented imaging system 264 includes a flow cell cuvette 266, a flow cell cavity 268, an illumination light 270, a first imaging sub-system 272, a first detector 274, second imaging sub-system 276, a second detector 278 and a processor 280. The first imaging sub-system 272 receives the first collected light from a second target object 282 and transmits first focused light 284 along a first optical axis 286 to be received by the first detector 274. The first focused light 284 has a first imaging sub-system best focused conjugate image for second target object (first image of second target) 288 with respect to the second target object 282. The first focused light 284 also has a first imaging sub-system best focused conjugate image for first target object (first image of first target) 290 with respect to a first target object 292 also in the flow cell cavity 268. The first collected light results from light either being emanated from luminous versions of the second target object 282 or coming from an incoherent or coherent light source and being scattered or reflected off of the second target object. The second imaging sub-system 276 receives the second collected light from the second target object 282 and transmits second focused light 294 along second optical axis 296 to be focused at the second imaging subsystem best focused conjugate image for second target object (second image of second target) 298. For the implementation depicted in FIG. 23, the first optical axis 286 and the second optical axis 296 are orthogonal with respect to one another.

With respect to the example shown in FIG. 23, the second target object 282 and the first target object 292 occupy the same position with respect to the direction of the first optical axis 286. However, with respect to the direction of the second optical axis 296, the first target object is closer to the second imaging sub-system 276 than is the second target object. As shown in FIG. 23, a first lateral shift 300 exists between the first image of second target 288 and the first image of first target 290 along the surface of the first detector 274 since the second target object 282 and the first target object 292 occupy the same position with respect to the first optical axis 286 and not with respect to the orthogonal second optical axis 296. As shown in FIG. 23, the second detector 278 is located with respect to the best focus position for the first target object 292.

Since the second target object 282 is farther away than the first target object 292 from the second imaging sub-system 276, the second image of second target 298 is located a focus shift for second imaging sub-system image 302 from the second detector 278.

Due to the orientation between the first imaging sub-system 272 and the second imaging sub-system 276, the focus shift for second imaging sub-system image 302 is proportional to the first lateral shift 300. In some implementations, the processor 280 is communicatively linked by communication links 503 to the first detector 274 and/or the second detector 278 to determine lateral displacements such as the first lateral shift 300. The processor 280 can further be communicatively linked by the communication links 503 to the first detector 274, second detector 278, the first imaging sub-system 272, and/or the second imaging sub-system 276 to either adjust the position of the first detector or the second detector, or adjust optical characteristics of the first imaging sub-system or the second imaging sub-system based upon determined displacements to correct for focus shifts such as the focus shift for second imaging sub-system image 302. For instance, as illustrated in FIG. 23, the processor 280 could determine that the first lateral shift 300 occurred as the first focused light 284 moved from first image of first target 290 to the first image of second target 288 as the flow cell cavity 268 first contained the first target object 292 and then contained the second target object 282. As a consequence of this determination, the processor 280 would instruct the second imaging sub-system 276 to move the second image of second target 298 to the second detector 278 based upon the first lateral shift 300. Alternatively, the processor 280 would instruct the second detector 278 to move to the current position of the second image of second target 298 as shown in FIG. 23.

Figure 24:
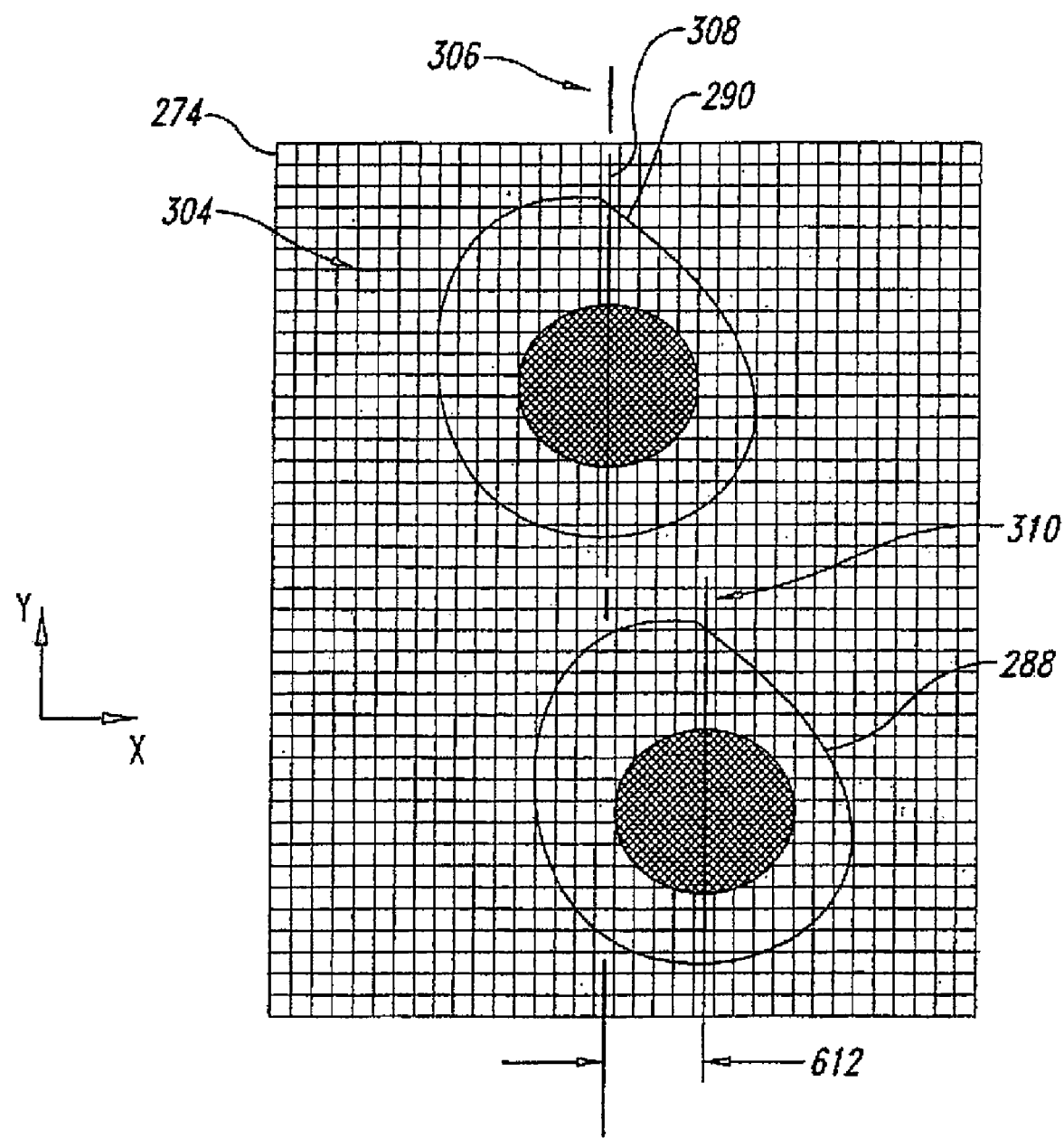
FIG. 24 is a schematic illustrating an exemplary set of images projected on one of the detectors of the two-dimensional imaging system, as shown in FIG. 23.

The relationship between lateral shifts, such as the first lateral shift 300, and focus shifts, such as the focus shift for second imaging sub-system image 302, is further elaborated by use of FIG. 24 showing a representative example of the first detector 274 having a plurality of a first detector picture element 304, each being approximately 10 microns in size, in this representative example, arranged in rows and columns. The first image of first target 290 of the first target object 292 is shown as an exemplary cell having a cytoplasm and cell nucleus. Since the first target object 292 is in focus at the second image of second target 298, the lateral position along the x-axis of the centroid of first image of second target 308 of its first image of first target 290 defines the location of the ideal focal plane for an orthogonal axis 306 along the y-axis on the first detector 274. The first image of second target 288 of the second target object 282 is also shown as a cell having a cytoplasm and cell nucleus. Since the second target object 282 is not positioned at the ideal focal plane for the second detector 278, the second target object is imaged off-axis on the first detector 274 and a centroid of first image of first target 310 and of its first image of second target 288 exhibits the first lateral shift 300 in position from the on-axis of the first image of first target 290 of the first target object 292. The amount of lateral shift between images at the first detector 274 is determined by the separation of objects, such as the first target object 292 and the second target object 282, and the lateral magnification of the first imaging sub-system 272. The amount of defocus between images at the second detector 278 is determined by the separation of the objects and the magnification along the second optical axis 296 or the longitudinal magnification of the second imaging sub-system 276. It is to be noted that the longitudinal magnification of the optical system in these examples is equal to the square of the lateral magnification.

In a typical implementation, magnification of optical systems such as the first imaging sub-system 272 in the second imaging sub-system 276 is 10×, with a pixel size on the detectors, such as the first detector 274 and the second detector 278, being 10 microns. In FIG. 24, a five pixel or 50 micron positive lateral shift along the x-axis on the first detector 274 for the centroid of first image of first target 310 is shown. In this representative example, given a 10× magnification, a 50 micron positive lateral shift along the x-axis translates into a five micron shift along the optic axis, such as the second optical axis 296, away from the second imaging sub-system 276. In order to correct focus, the second detector 278 should be moved approximately 500 microns (five micron error×lateral magnification×lateral magnification) toward the second imaging sub-system 276. In these implementations, centroids, such as the centroid of first image of second target 308 and the centroid of first image of first target 310, are calculated using conventional methods. Some implementations keep a running average of multiple cell centroid locations to normalize any inconsistencies in cell shape before instructing an electromechanical system associated with either the detectors, such as the first detector 274 and the second detector 278, or optical subsystems, such as the first imaging sub-system 272 and the second imaging sub-system 276, for correction of focus error.

In general, information from each of the imaging sub-systems, such as the first imaging sub-system 272 in the second imaging sub-system 276, may be used to correct focus of one another. The target objects, such as the second target object 282, the first target object 292, and other target objects including other types of cells, do not need to lie along one of the optical axes of the imaging sub-systems, such as the first optical axis 286 and the second optical axis 296 in order to determine centroids of the target objects and to ascertain lateral shift. Implementations are used with magnification at various levels as long as corresponding lateral displacements are properly translated into focus error and subsequently proper correction is implemented. Many sorts of elements conventionally known can be translated in order to correct for focus error; therefore, the representative examples related to these implementations are not meant to be limiting. In other implementations, other types of detectors are used such that images of the target objects are not created, but rather only centroids are computed that are indicative of the position of the one or more target objects in the flow cell cavity 268.

As in the un-polarized implementations of the imaging system 100, it is important to control the amount of light in each beam path in order to result in images of approximately the same intensity level at the detector. In addition to the methods previously discussed for light control, in the polarized implementations, the light intensity in the defocus optical path 138 can also be controlled by the angular orientation of the optical retardation plate 212. As the optical retardation plate is rotated the plane of linear polarization also rotates. This results in the second polarization state vector 214 at the polarization beam splitter 208 to be rotated with respect to the plane of incidence so that polarization beam splitter optical coating 116 splits the incident light into its vector component s- and p-polarization states. Since the p-polarized light is transmitted through the polarization beam splitter optical coating 116 while the s-polarized light is reflected, the 2R defocused light 168 is reduced in intensity. The effective beam splitter ratio at the polarization beam splitter 208 can therefore be varied in this manner. An alternative to the use of neutral density filters in the polarized embodiment is the use of a linear polarizer as a variable transmittance filter. When placed in the linear polarized first transmitted light 136 or the first reflected light 138, the transmittance of the light through the polarizer will vary with the orientation of the polarizer axis.

Figure 25:
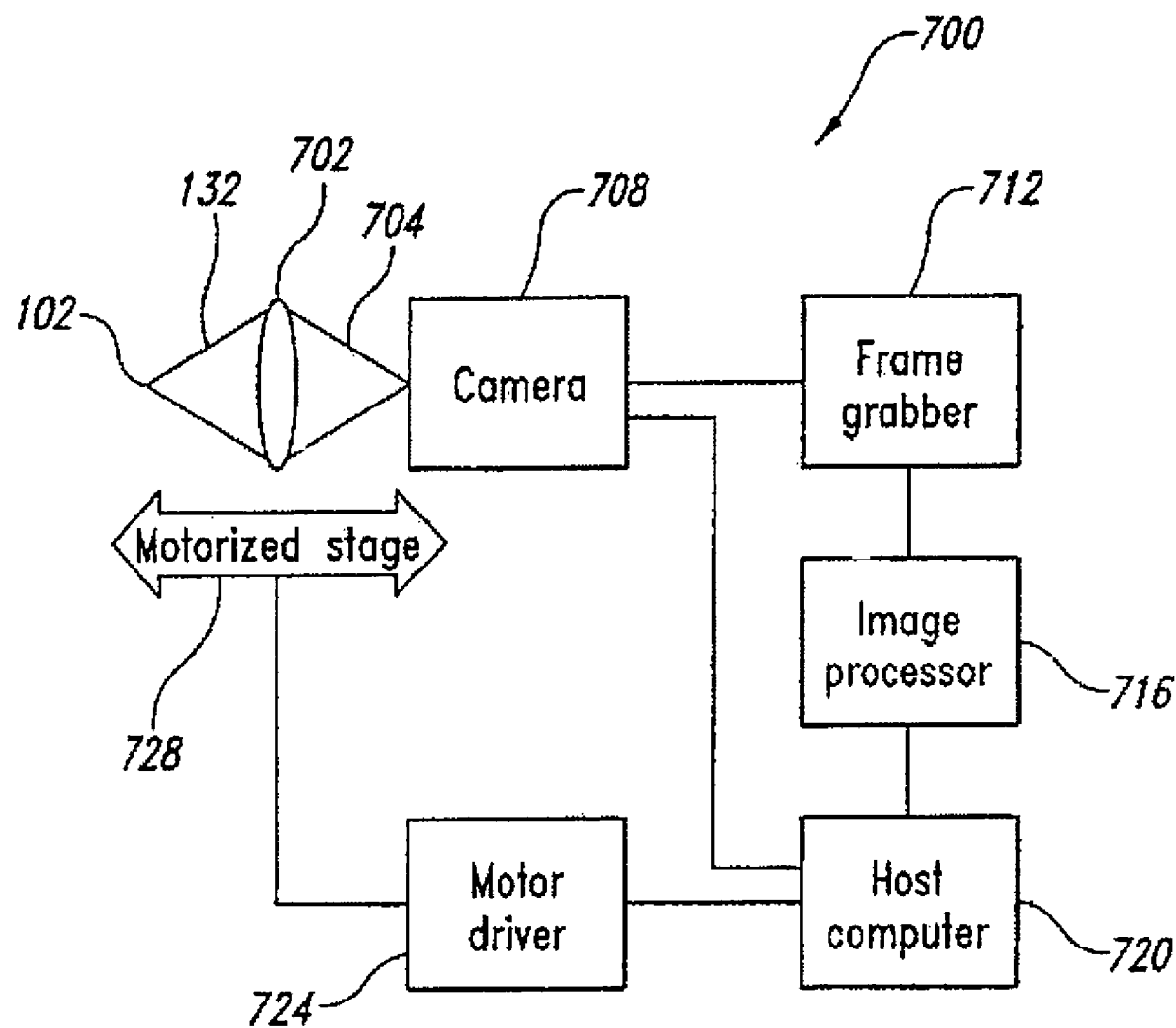
FIG. 25 is a schematic illustrating an alternative implementation of the imaging system, as shown in FIGS. 2-3, FIGS. 6-9, FIGS. 13-15, FIGS. 17-18, and FIGS. 20-21.

An active autofocus system 700 is illustrated in FIG. 25 to receive from an optical system 702 such as an implementation of the imaging system 100, light 704 by a camera 708. The host computer 720 runs an auto focus system software having a method such as described below. Object light 132 is collected from the target object 108 and imaged by the optical system 702 onto the camera 708. Light 704 from the optical system is brought to a focus at the camera 708 with the precise focal position under control involving a frame grabber 712, an image processor 716, a host computer 720, a motor driver 724, and a motorized stage 728. The motorized stage 728 may be configured to move the entire optical system 700 or any number of optical components of the optical system, such as the camera 708. Alternatively, the motorized stage 728 could be configured to move the target object 102. The host computer 720 controls image acquisition by the camera 708. The frame grabber 712 executes methods for image processing 716, which result in instructions based on one or more auto-focus error signals being sent to the motor driver 724 to move the motorized stage 728 the appropriate magnitude and direction so as to maintain objects in focus at the camera.

Figure 26:
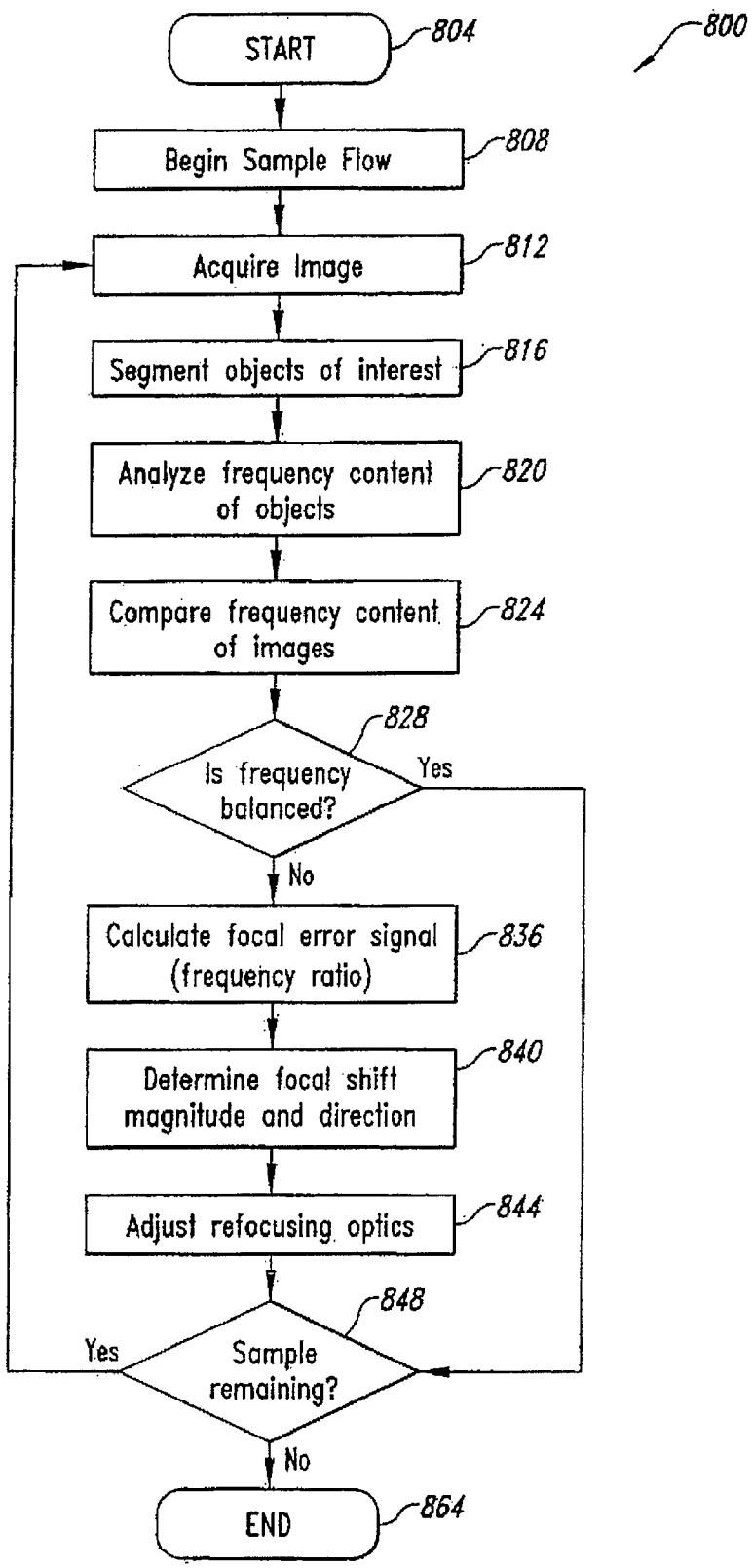
FIG. 26 is a flowchart illustrating a method used by alternative implementation of the imaging system, as shown in FIG. 25.

A method 800 for maintaining objects in focus using the active autofocus system 700 is shown in FIG. 26. The method 800 works in conjunction with the optical system 702, such as the imaging system 100 wherein in the imaging system produces imagery such as described with respect to a detector, such as the first detector 120, shown in FIG. 16 having two focus areas, such as the 2T1T focus area 224 and the 2R defocused area 232. Imagery is used by the method 800 to produce a focus error signal used to control the position of an adjustable optical component of the autofocus system 700, as described above, to maintain the imagery in focus. The method 800 begins with sample flow being initiated (step 808) and an image being acquired (step 812).

Segmentation processes are used to identify objects of interest (e.g. cells) in the two focus areas (step 816). For these segmented objects, their frequency content is analyzed for each image column (focal plane) (step 820) and compared with each other (step 824) to determine whether the frequency content is balanced, e.g. when the system is in focus. If the frequency content is balanced (YES branch of decision step 828), the system is in focus and no focus correction is required, so the method 800 determines whether additional samples remain and if not (NOT branch of decision step 848) ends. Otherwise (YES branch of decision step 848) goes back to step 812. If the frequencies are not balanced (NO branch of decision step 828), a focus error signal is determined (step 836) (e.g., from the ratio of frequency content) and the required focal shift magnitude and direction is determined (step 840) by reference to a database of stored correction factors or a look-up table. The refocusing optics are then adjusted (step 844) in the proper direction by the required amount and step 848 is executed as described above.

Figure 27:
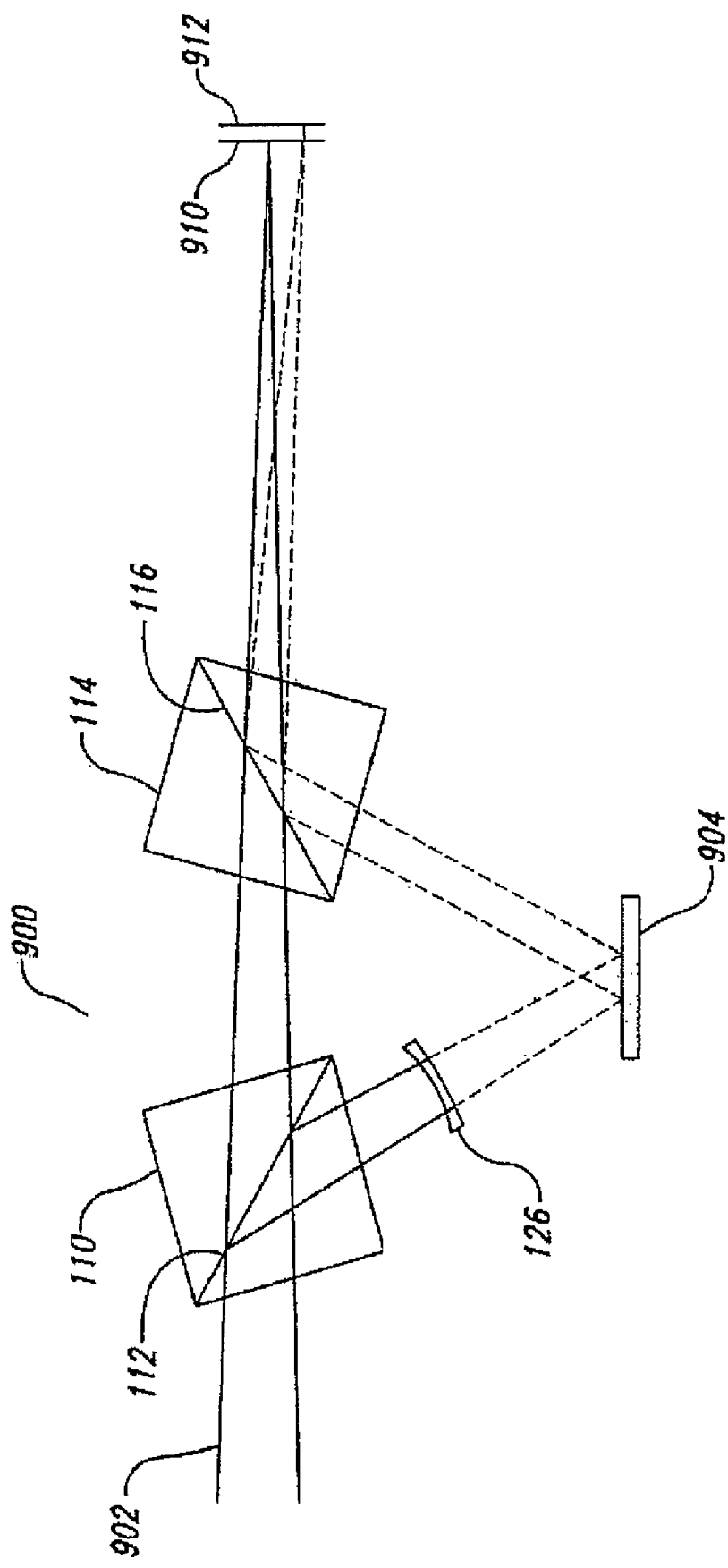
FIG. 27 is a schematic illustrating an alternative implementation of the imaging system, as shown in FIGS. 2-3, FIGS. 6-9, FIGS. 13-15, FIGS. 17-18, FIGS. 20-21 and FIG. 25.

An alternative implementation 900 of the imaging system 100 is illustrated in FIG. 27 wherein one reflector 904 is used to reflect light in the defocus optical path 122. In this exemplary illustration of the alternative implementation, converging light 902 is received by the amplitude beam splitter 110 and is partially reflected and partially transmitted. The portion of the converging light 902 that is partially reflected is first defocused through the defocus system 126 and then reflected by a reflector 904 on to the amplitude beam splitter 114 to be partially reflected as defocused light 908. The portion of the converging light 902 that is partially transmitted by the amplitude beam splitter 110 is also partially transmitted by the amplitude beam splitter 114 as unaltered light 906.

Figure 28:
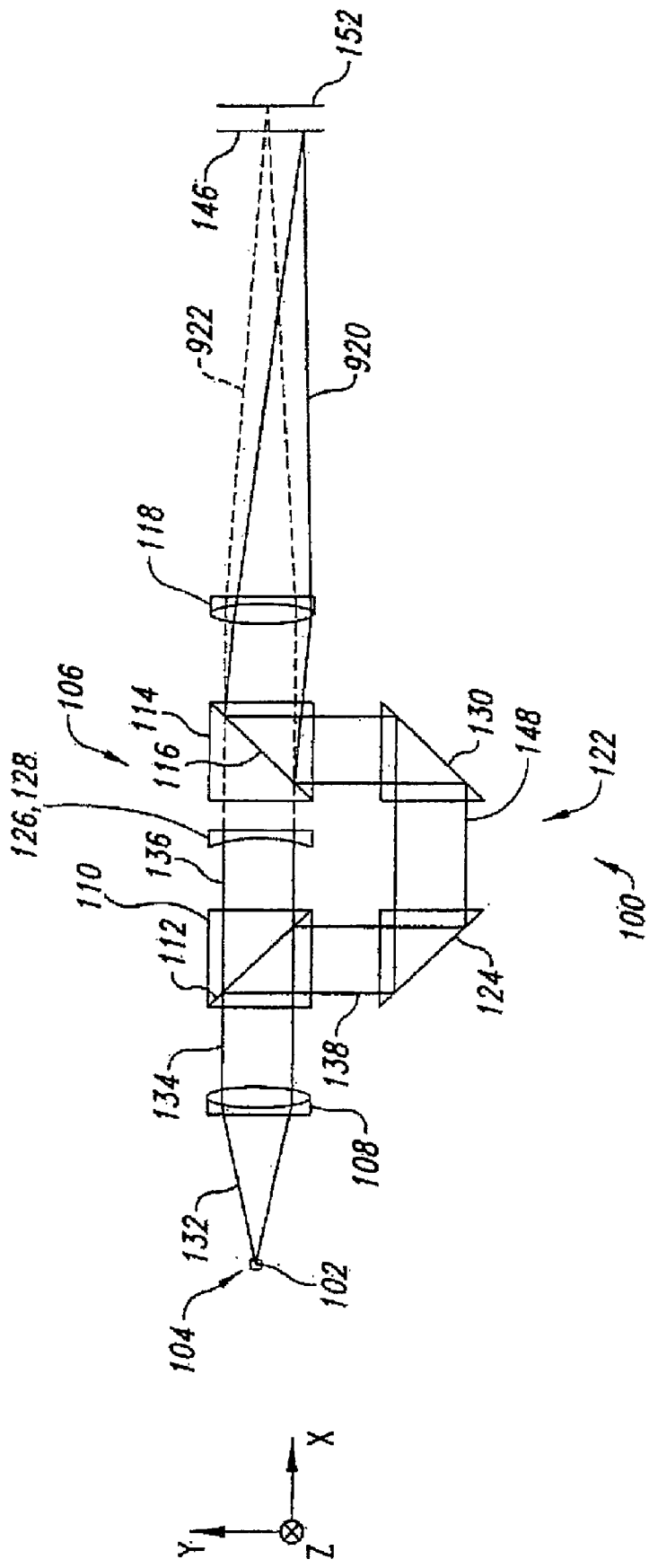
FIG. 28 is a schematic illustrating an alternative implementation of the imaging system, as shown in FIGS. 2-3, FIGS. 6-9, FIGS. 13-15, FIGS. 17-18, FIG. 20-21, FIG. 25, and FIG. 27.

An exemplary implementation of the imaging system is illustrated in FIG. 28 showing the defocus system 126 positioned in the transmission path of the amplitude beam splitter 110. As a result, unaltered light 920 and defocused light 922 have reversed positions compared to other implementations described above. In other implementations using other aspects described above, including but not limited to polarization aspects, dispersion aspects, bi-orientation aspects, and aspects directed to other multiple detector configurations, the defocus system 126 is also positioned in a transmission path rather than a reflected path.

The numerical aperture, NA, of a microscope objective lens is given by n*sin θ where n is the index of refraction of the medium in which the object lies and θ is the half angle of the cone of collected light. The depth of focus of an optical system is the distance through which a detector can be moved along the optical axis forward and backward from focus before the image appears to be out of focus. For a diffraction-limited lens such as a well-corrected microscope objective, Rayleigh's criterion for tolerable defocus allows for λ/4 wave of wave front error where λ is the wavelength of the image forming light. This translates to an allowable depth of focus at the image of $$D'=\lambda/(NA')^2$$

where NA' is the numerical aperture on the image side of the objective. For a system with lateral magnification m, NA'=NA/m and $$D'=m^2*\lambda/(NA)^2$$

where NA is the numerical aperture on the object side of the objective. The depth of field, D, is related to the depth of focus by the longitudinal magnification of the system, $m^2$, so that $D=D'/m^2$ or $$D=\lambda/(NA)^2$$

For an oil immersion type objective the index of refraction of the oil must be accounted for and the depth of field is n times larger than the above.

High numeric aperture microscope objectives used with some of the implementations of the imaging system 100 are readily available commercially with NA values ranging from 0.5 to 1.4. For visible light imaging, assuming a center wavelength of λ=0.55 microns, these NA values translate to tolerable depths of field from as little as 0.4 microns to 4.0 microns. Tolerances for allowable depth of focus other than Rayleigh's criterion may result in an expansion or reduction of this range. For example, a decrease in the modulation transfer function at a particular spatial frequency might be the acceptance criterion for implementation of the imaging system 100.

In some implementations of the imaging system 100 for biological cell imaging in flow, collection lens are microscope objectives of 40× magnification with 0.9 NA and the imaging lens has a focal length of 200 mm. Cell objects are nominally 10 microns in diameter and the imaging field of view orthogonal to the flow axis is set to be 30 microns. Detector pixel size is approximately 13 microns. Consequently, the desired lateral separation between unaltered and defocused focal plane images at the detector is 100 pixels or 1.3 mm. The lateral separation at the detector is given by f*tan φ, where f is the focal length of the imaging lens and φ is the optical angle of separation. For the 200 mm focal length lens, the angle of separation is 6.5 milliradians to achieve the 1.3 mm lateral separation. Note that this translates to a mechanical angle of 3.25 milliradians for the beam combiner element, since upon reflection the optical angle is twice the mechanical angle of the reflective surface. The depth of field for the 0.9 NA objective is 1.03 microns and the required optical power introduced into the defocused optical path is ±0.04 diopter, corresponding to a defocus lens focal length of ±25 meters. This optical power results in a separation of the unaltered and defocused object planes by 1 micron, to nearly double the depth of field of the system.

Numerous implementations of the imaging system 100 can be accomplished with a variety of components. In the biological application, objects are cells of typically 5 to 20 microns in diameter. In other implementations, microscopic objects of interest may have a size range of 1 to 50 microns. High NA microscope objectives are commercially available from 10×/0.5 NA to 100×/1.4 NA with optical designs optimized for use with imaging lens focal lengths of 165 to 200 mm. Typical CCD detector pixel sizes range from 5 to 25 microns. Optical systems employing these components in various embodiments may require optical power in the defocused optical path to range from ±0.01 to ±0.1 diopter. Angular separation between the unaltered and defocused optical paths may range from as little as 0.1 degree to 10 degrees. However, those skilled in the art will appreciate that other optical system applications with different imaging requirements can be constructed with custom designed components that may extend these typical parameter ranges.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. For imaging a target object, an imaging system comprising:
   (a) a first imaging sub-system comprising a light collection system positioned with respect to the target object in a first orientation, the first imaging sub-system configured to transmit a first image of the target object;
   (b) a first detector positioned to receive the first image of the target object at a first location on the first detector when the target object is in a first target location and to receive the first image of the target object at a second location on the first detector when the target object is in a second location different than the first location of the target object;
   (c) a second imaging sub-system comprising a light collection system positioned with respect to the target object in a second orientation different than the first orientation, the second imaging sub-system configured to transmit a second image of the target object at a best focus distance from the second imaging sub-system;
   (d) a second detector positioned to receive the second image of the target object; and
   (e) a processor communicatively linked to the first detector and configured to determine a distance between the first location on the first detector and the second location on the first detector, the processor communicatively linked to the second imaging sub-system and configured to transmit instructions to the second imaging sub-system based upon the determined distance between the first location on the first detector and the second location on the first detector, the second imaging sub-system configured to change the best focus distance from the second imaging sub-system based upon the instructions received from the processor to correct focus.

2. The system of claim 1, wherein the first orientation is along an x-axis and the second orientation is along a y-axis, the x-axis and the y-axis being substantially perpendicular to one another.

3. For imaging a target object in a flow stream, an imaging system comprising:
   (a) a first imaging sub-system comprising a light collection system positioned with respect to the target object in a first orientation, the first imaging sub-system configured to transmit a first image of the target object;
   (b) a first detector positioned to receive the first image of the target object at a first location on the first detector when the target object is in a first target location and to receive the first image of the target object at a second location on the first detector when the target object is in a second location
   (c) a second imaging sub-system comprising a light collection system positioned with respect to the target object in a second orientation, the second imaging sub-system configured to transmit a second image of the target object;
   (d) a second detector positioned a distance along an optical axis from the second imaging sub-system to receive light from the second imaging sub-system; and
   (e) a processor communicatively linked to the first detector, the processor configured to determine a distance between the first location on the first detector and the second location on the first detector, the processor communicatively linked to the second imaging sub-system, the processor configured to transmit instructions to the second imaging sub-system based upon the determined distance between the first location on the first detector and the second location on the first detector, the second imaging sub-system configured to change the distance that the second detector is positioned along the optical axis from the second imaging sub-system based upon the instructions received from the processor.

4. The system of claim 3, wherein the first imaging sub-system has a magnification and the instructions are based on the determined distance multiplied by the square of the magnification of the second imaging sub-system.

* * * * *